United States Patent
Albertsen et al.

(10) Patent No.: US 7,154,024 B2
(45) Date of Patent: *Dec. 26, 2006

(54) MALE TISSUE-PREFERRED REGULATORY SEQUENCES OF MS45 GENE AND METHOD OF USING SAME

(75) Inventors: Marc C. Albertsen, Grimes, IA (US); Timothy W. Fox, Des Moines, IA (US); Carl W. Garnaat, Ankeny, IA (US); Gary Huffman, Des Moines, IA (US); Timmy L. Kendall, Tucson, AZ (US)

(73) Assignee: Pioneer Hi-Bred, Inc., Johnston, IA (US)

( * ) Notice: Subject to any disclaimer, the term of this patent is extended or adjusted under 35 U.S.C. 154(b) by 257 days.

This patent is subject to a terminal disclaimer.

(21) Appl. No.: 10/713,381

(22) Filed: Nov. 14, 2003

(65) Prior Publication Data

US 2004/0221331 A1 Nov. 4, 2004

Related U.S. Application Data

(63) Continuation of application No. 09/504,487, filed on Feb. 15, 2000, now abandoned, which is a continuation-in-part of application No. 08/880,499, filed on Jun. 23, 1997, now Pat. No. 6,037,523.

(51) Int. Cl.
*C12N 15/09* (2006.01)
*C12N 15/82* (2006.01)
*A01H 5/00* (2006.01)

(52) U.S. Cl. .............. 800/287; 800/278; 800/298; 435/320.1; 435/468; 435/430; 536/24.1

(58) Field of Classification Search ............... 800/287, 800/278, 298, 295; 435/468, 430, 320.1; 536/24.1
See application file for complete search history.

(56) References Cited

U.S. PATENT DOCUMENTS

| | | | |
|---|---|---|---|
| 4,732,856 A | 3/1988 | Federoff | |
| 4,833,080 A | 5/1989 | Brent et al. | |
| 5,086,169 A | 2/1992 | Mascarenhas | |
| 5,168,053 A | 12/1992 | Altman et al. | |
| 5,190,931 A | 3/1993 | Inouye | |
| 5,208,149 A | 5/1993 | Inouye | |
| 5,356,799 A | 10/1994 | Fabijanski et al. | |
| 5,364,780 A | 11/1994 | Hershey et al. | |
| 5,412,085 A | 5/1995 | Allen et al. | |

(Continued)

FOREIGN PATENT DOCUMENTS

AU  4945690  8/1990

(Continued)

OTHER PUBLICATIONS

Kim et al. Plant Molecular Biology, 1994 vol. 24, pp. 105-117.*

(Continued)

*Primary Examiner*—Medina A. Ibrahim
(74) *Attorney, Agent, or Firm*—Patricia A. Sweeney

(57) ABSTRACT

The present invention relates to isolated male tissue-preferred regulatory sequences from Ms45 gene. The invention also relates to the use of Ms45 gene male tissue-preferred regulatory sequences in mediating male fertility in a plant, and in producing hybrid seed. The Ms45 male tissue-preferred regulatory region can be operably linked to exogenous genes encoding cytotoxins or inhibitory molecules. The invention also relates to plant cells, plant tissue and plants that contain the MS45 gene regulatory sequences.

12 Claims, 10 Drawing Sheets

U.S. PATENT DOCUMENTS

| | | | |
|---|---|---|---|
| 5,426,041 | A | 6/1995 | Fabijanski et al. |
| 5,432,068 | A | 7/1995 | Albertsen et al. |
| 5,470,359 | A | 11/1995 | Huffman |
| 5,472,841 | A | 12/1995 | Jayasena et al. |
| 5,477,002 | A | 12/1995 | Tuttle et al. |
| 5,478,369 | A | 12/1995 | Albertsen et al. |
| 5,545,546 | A | 8/1996 | Allen et al. |
| 5,589,610 | A | 12/1996 | De Beuckeleer et al. |
| 5,795,753 | A * | 8/1998 | Cigan et al. ................ 800/274 |
| 6,037,523 | A * | 3/2000 | Albertsen et al. ........... 800/287 |

FOREIGN PATENT DOCUMENTS

| | | |
|---|---|---|
| EP | 0329308 | 8/1989 |
| EP | 0420819 | 4/1991 |
| EP | 0465024 | 1/1992 |
| EP | 0754757 | 1/1997 |
| WO | WO 8910396 | 11/1989 |
| WO | WO 9008825 | 8/1990 |
| WO | WO 9012107 | 10/1990 |
| WO | WO 9109957 | 7/1991 |
| WO | WO 9211379 | 7/1992 |
| WO | WO 9218625 | 10/1992 |
| WO | WO 9302197 | 2/1993 |
| WO | WO 9318142 | 9/1993 |
| WO | WO 9318171 | 9/1993 |
| WO | WO 9413809 | 6/1994 |
| WO | WO 9425593 | 11/1994 |
| WO | WO 9640721 | 12/1996 |

OTHER PUBLICATIONS

Benfey et al (Science, 1990, vol. 250, pp. 959-966.*
Willing, R.P., et al.; "An Analysis of the Quantity and Diversity of Messenger RNA's from Pollen and Shoots of Zea Mays", *Theor. Appl. Genet.*; 75:751-753 (1988).
Stinson, et al.: "Genes Expressed in the Male Gametophyte of Flowering Plants and their Isolation", *Plant Physiol.*; 83:442-447 (1987).
Aarts, M.G.M., et al.; "Transposon Tagging of a Male Sterility Gene in Arabidopsis", *Nature*; 363:715-717 (1993).
Hanson, D.D., et al.; "Characterization of a Pollen Specified cDNA Clone from Zea Mays, and its Expression", *The Plant Cell*: 1:173-179 (1989).
McCormick, et al.; "Anther-Specific Genes: Molecular Characterization and Promoter Analysis in Transgenic Plants", Plant Reproduction: From Floral Induction to Pollination, Lord, et al., (eds)(1989) pp. 128-135.
Van der Meer, et al.; "Antisense Inhibition of Flavanoid Biosynthesis in Petunia Anthers Results in Male Sterility", *The Plant Cell*; 4:253 (1992).
Pareddy, D.R. and J.F. Petelino; "Tassel Culture of Elite Inbreds of Maize", *Crop. Sci. Journal*; 29:1564-1566 (1989).
Reznickova, C.R.; "Histochemical Study of Reserve Nutrient Substances in Anther of *Lilium candidum*", *Acad. Bulg. Sci.*; 31:1067 (1978).
Nave, et al.; "Enzymatic Changes in Post-meiotic Anther Development in *Petunia hybrida*. I. Anther Ontogeny and Isozyme Analyses". *J. Plant Physiol.*; 125:451 (1986).
Sawhney, et al.; "Enzymatic Changes in Post meiotic Anther Development in *Petunia hybridia*. II. Histochemical Localization of Esterase, Peroxidase, Malate- and Alcohol dehydrogenase", *J. Plant Physiol.*; 125:467 (1986).
Mepham, et al.; "Observation on the Fine Structure of Developing Microspores of Tradescantia bract ata", *Protoplasma*; 70:1 (1970).
Kaul; "Male Sterility in Higher Plants"; Monographs on Theoretical and Applied Genetics, vol. 10; Frankel, et al. (eds.): pp. 15-95 (Springer Verlag, 1988).
Warmker, et al.: Cytoplasmic Male Sterility in Sorghum, *J. Hered.*; 63:103 (1972).
Mariani, C., et al.; "Induction of Male Sterility in Plants by a Chimeric Ribonuclease Gene", *Nature*; 347:737-741 (1990).

Quaas, et al.; "Expression of the Chemically Synthesized Gene for Ribonuclease T1 in *Escherichia coli* Using a Secretion Cloning Vector". *Eur. J. Biochem.*; 173:617 (1988).
Hartley; "Barnase and Barstar. Expression of its Cloned Inhibitor Permits Expression of a Cloned Ribonuclease", *J. Molec. Biol.*; 202:913 (1988).
Wosnick, et al.; "Rapid Construction of Large Synthetic Genes: Total Chemical Synthesis of Two Different Versions of the Bovine Prochymosin Gene", *Gene*; 60:115 (1987).
Adang, et al.; "The Reconstruction and Expression of *Bacillus thuringiensis* cryIIIA gene in Protoplasts and Potato Plants", *Plant Molec. Biol.*; 21:1131 (1993).
Estruch, et al.; The Protein Encoded by the rolB Plant Oncogene Hydrolses Indole Glucosides, *EMBO J.*; 11:3125 (1991).
Spena, et al.; "Anther-specific Expression of the rolB gene of Agrobacterium rhizogenes Increases IAA Content in Anthers and Alters Anther Development and Whole Flower Growth", *Theor. Appl. Genet.*; 85:520 (1992).
Paterson, et al.; "Structural Gene Identification and Mapping by DNA mRNA Hybrid-Arrested Cell-Free Translation". *Proc. Natl. Acad. Sci. USA*; 74:4370 (1987).
Koes, et al.; "Cloning and Molecular Characterization of the Chalcone Synthase Multigene Family of Petunia Hybrida", *Gene*; 81:245 (1989).
Koes, et al.; "The Chalcone Synthase Multigene Family of Petunia Hybrida: Differential, Light-regulated Expression During Flower Development and UV Light Induction", *Plant Molec. Biol.*: 12:213 (1989).
Steinecke, et al.; "Expression of a Chimeric Ribozyme Gene Results in Endonucleolytic Cleavage of Target mRNA and a Concomitant Reduction of Gene Expression in Vivo", *EMBO J.*; 11:1525 (1992).
Perriman, et al.; "A Ribozyme that Enhances Gene Suppression in Tobacco Protolasts", *Antisense Research and Development*; 3:253 (1993).
Yuan, et al.; "Selection of Guide Sequences that Direct Efficient Cleavage of mRNA by Human Ribonulease P", *Science*; 263:1269 (1994).
Wang, et al.: "Transcriptional Repression in *Saccharomyces cerevisiae* by a SIN3-LexA Fusion Protein", *Mol. Cell Biol.*; 13:1805 (1993).
Garriga, et al.; "Nucleotide Sequence Analysis and Comparison of the Lex-A Genes from *Salmonella typhimurium, Erwinia caratovor, Pseudomonas aeruginosa* and *Pseudomonas putida*", *Mol. Gen. Genet.*; 236:125 (1992).
Guan, L. and J.G. Scandalios; Characterization of the Catalase Antioxident Defense Gene Cat1 of Maize, and its Developmentally Regulated Expression in Transgenic Tobacco, *Plant J.*; 3:527-536 (1993).
Close, P.S.; "Cloning and Molecular Characterization of Two Nuclear Genes for *Zea mays* Mitochondrial Chaperonin 60."; Iowa State University; Ames, Iowa; 1993; pp. 92. 128 (Dissertation).
Chasen, Rebecca; "A Meeting of the Minds on Maize", *The Plant Cell*; 6:920-925 (1994).
Albertsen, Marc C., et al.; "Tagging, Cloning, and Characterizing a Male Fertility Gene in Maize", Fourth Joint Meeting of The Botanical Society of America and the Canadian Botanical Association, Ames, Iowa; 1993, and *Am. J. of Bot.*; 80(1993).
Bell, E.A. and B.V. Chartwood (editors); "Secondary Plant Products", published by Springer-Verlag (Berlin), (1980) pp. 341-343.
Benfy, Philip N., et al.: "Regulated Genes in Transgenic Plants"; *Science*; 244:174-181 (1989).
Balcells, L., et al.; "Transposons as Tools for the Isolation of Plant Genes": *Tibtech*; vol. 9 (1991).
Chandlee, J.; "The Utility of Transposable Elements as Tools for the Isolation of Plant Genes"; *Physiologia Plantarum*; 79:105-115; Copenhagen (1990).
Chandler, V., et al.; "The *Mu* Elements of *Zea mays*"; *Advances in Genetics*: see preprint to appear at 30:1-73 (1992).
Hanson, D., et al.; "Characterization of a Pollen-Specific cDNA Clone from *Zea mays* and its Expression"; *The Plant Cell*; 1:173-179 (1989).
Herdenberger, F., et al.; "Isolation of Flower-Specific cDNA Clones from Sunflower"; *Plant Science*; 669:111-122 (1990).

Izawa, T., et al.; "Introduction and Transposition of Maize Transposable Element Ac in Rice"; *Mol. Gen. Genet.*; 227(3):391-396 (1991).

Mascarenhas, J.; "The Isolation and Expression of Pollen-Expressed Genes"; *Current Science*; 58(18): 1006-1015 (1989).

Pear, J. et al.; "Isolation and Characterization of a Fruit-Specific cDNA and the Corresponding Genomic Clone from Tomato"; *Plant Molec. Biol.*; 13:639-651: (1989).

Peterhans, A., et al.; "Intrachromosomal Recombination in Plants"; *The EMBO J.*; 9(11):3437-3445 (1990).

Raghaven, V.; "mRNAs and A Cloned Histone Gene Are Differentially Expressed During Anther and Pollen Development in Rice": *J.of Cell Sci.*: 92:217-229 (1989).

Reddy, A.S.M., et al.; "Molecular Cloning of cDNAs for Auxin-Induced mRNAs and Developmental Expression of the Auxin-Inducible Genes": *Plant Molec. Biol.*; 14:643-653 (1990).

Rommens, C., et al.; "A Transposon Tagging Strategy With Ac on Plant Cell Level and Heterologous Plant Species"; *Plant Sci.*; 74:99-106 (1991).

Schweinfest, C., et al.; "Subtraction Hybridization cDNA Libraries From Colon Carcinoma and Hepatic Cancer"; *Annal. Tech. Appl.*; 7:64-70 (1990).

Smith, A., et al.; "Identification and Characterization of Stamen- and Tapetum Specific Genes from Tomato"; *Mol. Gen. Genet.*; 222:9-16 (1990).

Sommer, H., et al.; Deficiens. A Homeotic Gene Involved in the Control of Lower Morphogenesis in *Antirrhinum majus*: The Protien Shows Homology to Transcription Factors; *EMBO J.*; 9(3):605-613 (1990).

Sotelo, J., et al.; "Cloning, Sequence Analysis, and Expression of a cDNA Encoding a Plastid Localized Heat Shock Protein in Maize": *Plant Physiol.*; 93:1321-1328 (1990).

Twell, D., et al.; "Isolation and Expression of an Anther-Specific Gene from Tomato"; *Mol. Gen. Genet.*; 217:240-245 (1989).

Weiland, I., et al.; "A Method for Difference Cloning: Gene Amplification Following Subtractive Hybridization"; *Proc. Nat'l Acad. Sci. USA*; 87:2720-2724 (1990).

Yoder, J.I., et al.; "Progress Towards Gene Targeting in Plants"; *Genetic Engineering*; vol. 13; Plenum Press, New York (1991).

Frova, C., et al.; "Isozyme and HSP Gene Expression During Male Gametophyte Development in Maize"; *Isozymes: Current Topics in Biological and Medical Research*; Genetics, Development, and Evolution 15:97-120 (1987).

Koller, B., et al.; "Inactivating the $\beta_2$ microglobulin locus in mouse embryonic stem cells by homologous recombination"; *Proc. Nat'l Acad. Sci. USA*; 86:8932-8935 (1989).

Albertsen, Marc, et al.; "Developmental Cytology of 13 Genetic Male Sterile Loci in Maize"; *Can. J. Genet. Cytol.*; 23:195-208 (1981).

Doring, H.P.: "Tagging Genes with Maize Transposable Elements. An Overview"; *Maydica*; 34:73-88 (1989).

Klein, T.M., et al.; "Factors Influencing Gene Delivery into Zea mays Cells by High-Velocity Microprojectiles"; *Biotechnology*; 6:559-563 (1988).

Klein, T.M., et al.; "Genetic Transformation of Maize Cells by Particle Bombardment"; *Plant Physiol.*; 91:440-444 (1989).

Lyznik, L. et al.; "Stable Co-Transformation of Maize Protoplasts with gus A and neo Genes"; *Plant Molec. Biol.*; 13:151-161 (1989).

Rhodes, C., et al.; "Genetically Transformed Maize Plants from Protoplasts"; *Science*; 240:204-207 (1988).

Wiegand, R., et al.; "Messenger RNA Encoding a Glutathion-S-Transferase Responsible for Herbicide Tolerance in Maize is Induced in Response to Safener Treatment"; *Plant Molec. Biol.*; 7:235-243 (1986).

Moffat, Anne Simon; "Excess Genetic Baggage Dumped"; *Science*; 254(5037):1457 (1991).

Paszkowski, Jerzy, et al.; "Gene Targeting in Plants"; *The EMBO J.*; 7(13):4021-4026 (1988).

Lechelt, Christa, et al.; "Isolation and molecular analysis of the maize P locus"; *Mol. Gen. Genet.*; 219:225-234 (1989).

Chen, Jychian, et al.; "Transposition of Ac From the P Locus of Maize into Unreplicated Chromosomal Sites"; *Genetics*; 117:109-116 (1987).

Chen, Jychian, et al.; "Molecular Analysis of Ac Transposition and DNA Replication"; *Genetics*; 130:665-676 (1992).

Stadler, L.J.; "On the Genetic Nature of Induced Mutations in Plants"; reprinted from the Proceedings of the Sixth International Congress of Genetics; 1:274-294 (1932).

Neuffer, M.G., et al.; "Paraffin Oil Technique for Treating Mature Corn Pollen with Chemical Mutagens"; *Maydica XXIII*; pp. 21-28 (1978).

Rao, B. Subra; "A Case of Genic Male Sterility Induced by Sodium Azide in Pearl Millet"; *Biol. Zentralbl*; 104:519-521 (1985).

Conger, B.V. et al.; "Mutagenic Effectiveness and Efficiency of Sodium Azide Versus Ethyl Methanesulfonate in Maize: Introduction of Somatic Mutations at the $yg_2$ Locus by Treatment of Seeds Differing in Metabolic State and Cell Polulation"; *Mutation Research*; 46:285-296 (1977).

Filippetti, A., et al.; "Improvement of Seed Yield in Vicia Faba L. By Using Experimental Mutagenesis II Comparison of Gamma-Radiation and Ethyl-Methane-Sulphonate (EMS) in Production of Morphological Mutants"; *Euphytica*; 35:49-59 (1986).

Thurling, N., et al.; "EMS Induction of Early Flowering Mutants in Spring Rape (*Brassica napus*)"; *Plant Breeding*; 108:177-184 (1992).

Foulkes, Nicholas, et al.; "More is Better: Activators and Repressors from the Same Gene"; *Cell*; 68:411-414 (1992).

Scheid, Ortrun M., et al.; "Reversible inactivation of a transgene in *Arabidopsis thatiana*"; *Mol. Gen. Genet.*; 228:104-112 (1991).

Brussian, Judy A., et al.; "An Arabidopsis Mutant with a Reduced Level of cab140 RNA is a Result of Cosuppression"; *The Plant Cell*; 5:667-677 (1993).

Holzmayer, Tatyana A., et al.; "Isolation of dominant negative mutants and inhibitory antisense RNA sequences by expression selection of random DNA fragments"; *Nucleic Acids Research*; 20(4):711-717.

Helene, Claude, et al.; "Specific regulation of gene expression by antisensce, sense and antigene nucleic acids"; *Biochimica at Biophysica Acta*; 1049:99-125 (1990).

Bourque, June E., et a.; "Suppression of gene expression in plant cells utilizing antisense sequences transcribed by RNA polymerase III"; *Plant Molec. Biol.*; 19:641-647; (1992).

Aarts, Mark G.M.; "Transposon tagging of a male sterility gene in *Arabidopsis*"; *Nature*; 363:715-171 (1993).

* cited by examiner

```
                        NotI       BamHI
                         |          |
-209                    GCGGCCGC GGATCCCGTG TCATCTCACA TGGCATACTA
                                 GCGC GGGCCCGCGC
                                      LS01
                                                     GCCGGGCCCG
                                                     LS02

-171    CATGCTTGTT CAACCGTTCG TCTTGTTCCA TCGTCCAAGC CTTGCCTATT
        GCGCGGGCCC
          LS03     GCGGGCCCGC
                     LS04      CGGGCCCGGC
                                 LS05       CGCGGGCCCG
                                              LS06      GCGCGGGCCC
                                                          LS07

-121    CTGAACCAAG AGGATACCTA CTCCCAAACA ATCCATCTTA CTCATGCAAC
        GGCCGGGCCC
          LS08     GCCGGGGCCC
                     LS09      GCGGGCCCGC
                                 LS10      GCGGGGGCCC
                                             LS11     GGGCCCGCCG
                                                        LS12
                                  BglII
                                    |
-71     TTCCATGCAA ACACGCACAT ATGTTTCCTG AACAGATCTA TTAAAGATCA
        CGGGCCCGCG
          LS13     CGGGCCCGCG
                     LS14      GGGCCCGGCC GCG
                                  LS15

-21     CAACAGCTAG CGTTCTCCCG CTAGCTTCCC TCTCTCCTCT GCCGATCTTT

NcoI
                      |
+30     TTCGTCCACC ACCATGG
                                                      FIG.8
```

MALE TISSUE-PREFERRED REGULATORY SEQUENCES OF MS45 GENE AND METHOD OF USING SAME

This application is a continuation of U.S. Ser. No. 09/504,487, filed Feb. 15, 2000, now abandoned, which is a CIP of U.S. Ser. No. 08/880,499, filed Jun. 23, 1997, now U.S. Pat. No. 6,037,523.

FIELD OF THE INVENTION

The present invention is related to isolated DNA sequences which act as regulatory regions in eukaryotic cells. More specifically, the present invention is related to isolated DNA sequences from maize which act as male tissue-preferred regulatory regions and play a role in the expression of genes in male tissues. The present invention is also directed to a method for conferring on a gene, which may or may not be normally expressed in male tissues, the ability to be expressed in a male tissue-preferred manner.

BACKGROUND OF THE INVENTION

Tissue- and temporal-specific gene expression and regulation are found, inter alia, during sexual reproduction in eukaryotes. In plant gametogenesis, important cytological and biochemical changes occur during pollen development when the asymmetric mitotic division of the haploid microspore results in the formation of two cells; each with different developmental fates. The vegetative cell supports pollen growth while the generative cell undergoes mitosis and develops into sperm cells. Messenger RNAs specific to both pathways within pollen have been identified in plants such as maize, tomato, tobacco, rice and pansy; and messages specific to pollen or to one or more other cell types within anther such as tapetum, epidermis and stomium have also been identified.

Pollen gene expression during differentiation involves an estimated 24,000 genes (Willing, et al., "An Analysis of the Quantity and Diversity of mRNA's From Pollen and Shoots of *Zea mays*"; *Theor. Appl. Genet.*; Vol. 75; pp. 751–753; (1988)), however only 10% of clones from a cDNA library are male-specific (Stinson, et al., "Genes Expressed in the Male Gametophyte and Their Isolation"; *Plant Physiol.*; Vol. 83; pp. 442–447; (1987)) and the percentage of genes expressed in pollen that are pollen-specific is between 5% and 80% (Willing, et al., "An Analysis of the Quantity and Diversity of mRNA's From Pollen and Shoots of *Zea mays*"; *Theor. Appl. Genet.*; Vol. 75; pp. 751–753; (1988)). This complex process of microsporogenesis involves the sequential production of many gene products.

To date male-specific genes have been cloned from plants: two of these, the maize Ms45 gene (U.S. Pat. No. 5,478,369) and the *Arabidopsis* Ms2 gene (Mark, G. M., et al., *Nature*; Vol. 363; pp. 715–717; (1993)), have been shown to be required for pollen development. Other examples of male-specific promoters in plants include ZM13, PG, SGB6, and 5126.

The Zm13 promoter is disclosed in U.S. Pat. No. 5,086,169. It consists of 1315 base pairs and is from a pollen specific gene described by Hanson, et al., *Plant Cell*; Vol. 1; pp. 173–179; (1989). This gene hybridizes to mRNA found only in pollen.

Another pollen-specific promoter has been isolated and characterized upstream of the pollen-specific polygalacturonase gene (PG) U.S. Pat. No 5,412,085. This promoter region encompasses 2687 base pairs and is expressed predominantly in pollen and emergent tassel, but not in pre-emergent tassel. U.S. Pat. No. 5,545,546, also from Allen and Lonsdale, describes another pollen-specific promoter from the maize polygalacturonase gene. It is only expressed in pollen and in emergent tassel.

U.S. Pat. No. 5,470,359 describes a regulatory region from the SGB6 gene of maize which confers tapetum specificity. The tissue of expression, the tapetum, is a layer of cells that surrounds the microsporogenous cells in the anther and provides nutrients thereto.

The regulatory region of 5126 is described in U.S. Pat. No. 5,837,851. This promoter preferentially expresses in the anther region of the plant.

Nine anther-specific cDNA and genomic clones from tobacco are described in U.S. Pat. No. 5,477,002. The cDNA clones were anther-specific by Northern analysis, yet differed in developmental profiles. Clone Ant32 is tapetal-specific.

European Pat. No. 0 420 819 A1 describes the method of producing male sterile plants with the wun1 gene.

PCT WO 90/08825 describes anther-specific cDNAs TA13, TA26 and TA29 and their use in a male sterility system.

PCT WO 90/08825 explains male-sterility genes pMS10, pMS14 and pMS18 and their use with the GUS reporter gene.

U.S. Pat. No. 5,589,610 details a promoter corresponding to anther-specific cDNA and anther-preferred cDNA AC444.

The use of a plant promoter and an exogenous gene to effect a change in the genetic make-up of plants is known in the art (U.S. Pat. Nos. 5,432,068, 5,412,085, 5,545,546, 5,470,359 and 5,478,369) These patents discuss plant expression cassettes with a tissue-specific promoter linked to a gene to effect male sterility, fertility or otherwise express a gene in a specific tissue. However, these patents do not teach the use of this male tissue-preferred regulatory region or the use of this male tissue-preferred regulatory region with an exogenous gene as a method of controlling male sterility.

The present invention is directed to a male tissue specific regulatory region and methods of using the same. Expression of an exogenous gene in a male tissue-preferred manner can mediate male fertility and is useful in many systems such as in hybrid seed production.

SUMMARY OF THE INVENTION

It is an object of the present invention to provide a method for expressing exogenous genes in a male tissue-preferred manner using an expression vector that confers male tissue-preferred expression to an exogenous gene. This process may be used to restore (as in a male sterility system) or to otherwise impact fertility, as in hybrid seed production. It is a further object of this invention to provide a DNA regulatory region that confers male tissue-preferred gene expression. It is also an object of this invention to provide a male tissue-preferred regulatory region or those with sequence identity thereto preferably of about 70%, 75%, or 80%, more preferably of about 85%, or 90%, and most preferably of about 95% or 99%.

It is an object of this invention to provide an isolated nucleic acid sequence encoding the Ms45 male tissue-preferred regulatory regions.

It is an object of this invention to provide an isolated nucleic acid sequence encoding an Ms45 male tissue-preferred regulatory region from *Zea mays* comprising a nucleic acid sequence shown in SEQ ID NO: 1 or those with sequence identity thereto and fragments thereof that retain male tissue preferred expression. It is also an object of this invention to provide an isolated nucleic acid sequence encoding a Ms45 male tissue-preferred regulatory region from *Zea mays* comprising a nucleic acid sequence shown in SEQ ID NO: 2 or those with sequence identity thereto and fragments thereof that retain male tissue preferred expression.

An object of the invention is to provide important or essential regulatory regions of the MS45 promoter which may be used in the control of male tissue preferred expression of a gene.

It is an object of this invention to provide a recombinant expression vector comprising the isolated nucleic acid sequence shown in SEQ ID NO: 1, or those with sequence identity thereto, and fragments thereof operably linked to a nucleotide sequence encoding an exogenous gene such that said nucleotide sequence is expressed in a male tissue-preferred manner in such a way that it promotes the expression of the exogenous gene.

It is an object of this invention to provide an exogenous gene, wherein said exogenous gene is Ms45.

It is an object of this invention to provide a method of producing a transformed plant that expresses an exogenous nucleotide sequence in a male tissue-preferred manner comprising the steps of introducing into a plant said exogenous nucleotide sequence operably linked to a male tissue-preferred regulatory region comprising a nucleotide sequence which is shown at SEQ ID NO: 1 or those with sequence identity thereto and fragments thereof. The method wherein said introduction step may be performed by microprojectile bombardment, may utilize *Agrobacterium* or a transfer vector comprising a Ti plasmid. Also, there may be more than one copy of said exogenous nucleotide sequence operably linked to a male tissue-preferred regulatory region.

It is an object of this invention to provide a method wherein said regulatory region expresses in a male tissue-preferred manner in tissues selected from the group consisting of pollen, tapetum, anther, tassel, pollen mother cells and microspores.

It is an object of this invention to provide a transformed plant expressing an exogenous nucleotide sequence in a male tissue-preferred manner having an exogenous nucleotide sequence operably linked to a male tissue-preferred regulatory region shown at SEQ ID NO: 1 or SEQ ID NO: 2, those with sequence identity thereto and fragments thereof. Said plant is a monocot or a dicot. Any plant capable of being transformed may be used, including, for example, maize, sunflower, soybean, wheat, canola, rice and sorghum. This invention also provides the transformed tissue of the transformed plant. By way of example, the tissue may be pollen, ears, ovules, anthers, tassels, stamens pistils and plant cells. The transformed plant may contain more than one copy of said exogenous nucleotide sequence operably linked to a male tissue-preferred regulatory region.

It is an object of this invention to provide a method of mediating fertility in a plant wherein the male tissue-preferred regulatory region expresses said exogenous nucleotide sequence such that fertility is impacted. This exogenous nucleotide sequence can be any sequence impacting male fertility and can be, by way of example, a complementary nucleotidic unit encoding such antisense molecules as callase antisense RNA, barnase antisense RNA and chalcone synthase antisense RNA, Ms45 antisense RNA, or ribozymes and external guide sequences, or aptamers or single stranded nucleotides. The exogenous nucleotide sequence can also encode auxins, rol B, cytotoxins, diptheria toxin, DAM methylase, avidin, or may be selected from a prokaryotic regulatory system. Also, this exogenous nucleotide sequence is a male sterility gene or the Ms45 structural gene and this plant is a monocot or a dicot.

It is an object of this invention to provide a method of producing hybrid seed, comprising planting in cross pollinating juxtaposition, a male fertile plant and a male infertile plant produced according to the method above, allowing said cross pollination to occur and harvesting the resulting seed. The plants can be maize plants.

In another embodiment of the invention, it is possible for the gene impacting male fertility to be hemizygous dominant, that is where a single allele causes sterility or heterozygous dominant, where there are two alleles, with one allele causing sterility. This can be useful in certain situations where, for example, the avidin or streptavidin gene is the gene impacting male fertility. In such an instance, it is desirable to provide for the hybrid seed to segregate for fertility, in order to provide pollen for pollination in the farmer's field.

These and other objects are achieved, in accordance with one embodiment of the present invention by the provision of an isolated DNA molecule wherein the DNA molecule comprises a nucleotide sequence shown at SEQ ID NO: 1, SEQ ID NO: 2, those with sequence identity thereto and fragments thereof that retain the male tissue preferred expression of a gene.

In accordance with a further embodiment of the present invention, there has been provided an expression vector comprising an exogenous gene, wherein the expression of the exogenous gene is under the control of a male tissue-preferred regulatory region, and where the product of the exogenous gene impacts male fertility.

In accordance with a further embodiment of the present invention, there has been provided a method of using such an expression vector to produce a male-sterile plant, comprising the step of introducing an expression vector into plant cells, wherein the exogenous gene of the expression vector may be a complementary nucleotidic unit such as antisense molecules (callase antisense RNA, barnase antisense RNA and chalcone synthase antisense RNA, Ms45 antisense RNA), ribozymes and external guide sequences, an aptamer or single stranded nucleotides. The exogenous nucleotide sequence can also encode auxins, rol B, cytotoxins, diptheria toxin, DAM methylase, avidin, streptavidin, or may be selected from a prokaryotic regulatory system.

In accordance with a further embodiment of the present invention, there has been provided a method of using a male tissue-preferred regulatory region to produce a male-fertile hybrid plant comprising the steps of:

a) producing a first parent male-sterile plant comprising an expression vector that comprises a male tissue-preferred regulatory region and a first exogenous gene, wherein the male tissue-preferred regulatory region controls the expression of the first exogenous gene, and wherein the product of the first exogenous gene disrupts male fertility.

b) producing a second parent plant comprising an expression vector that comprises a second exogenous gene, wherein the regulatory region controls the expression of the second exogenous gene so that it can be expressed in male tissues;

c) cross-fertilizing the first parent with the second parent to produce a hybrid plant, wherein the male tissues of the hybrid plant express the second exogenous gene, and wherein the product of the second exogenous gene prevents the disruption of male tissue function by the product of the first exogenous gene, thereby producing a male-fertile hybrid plant.

In accordance with a further embodiment of the present invention, there has been provided a method of using a male tissue-preferred regulatory region to produce a male-fertile hybrid plant comprising the steps of:
a) producing a first parent male-sterile plant wherein a first gene involved in expression of male fertility is disrupted;
b) producing a second parent plant comprising an expression vector that comprises a male tissue-preferred regulatory region and an exogenous gene wherein the male tissue-preferred regulatory region controls the expression of the exogenous gene so that it can be expressed in male tissues and could functionally complement the function of the gene disrupted in a);
c) cross-fertilizing the first parent with the second parent to produce a hybrid plant, wherein the male tissues of the hybrid plant express the exogenous gene, and wherein the product of the exogenous gene prevents the disruption of the tassel function, thereby producing a male-fertile hybrid plant.

In still another embodiment of the invention, a method or producing a hybrid plant producing seeds with one or more grain or seed traits of interest is provided, such as improved oil, starch or protein composition, including the steps of:
a) producing a first male-sterile plant comprising an expression vector that comprises a male tissue-preferred regulatory region and a first exogenous gene, wherein the male tissue-preferred regulatory region controls the expression of the first exogenous gene, and wherein the product of the first exogenous gene disrupts male fertility;
b) producing a second plant which does not contain the first exogenous gene;
c) cross-fertilizing the first plant with the second plant to produce a hybrid first parent plant;
d) producing a second parent plant comprising an expression vector that comprises a second exogenous gene expressing a grain or seed trait of interest;
e) cross-fertilizing the first parent plant with the second parent plant thereby producing a hybrid plant which produces grain having the grain or seed trait of interest.

BRIEF DESCRIPTION OF THE DRAWINGS

FIG. 8 identifies mutations introduced by linker scanning mutagenesis into the region upstream of the MS45 promoter (SEQ ID NO: 1 or 2). (The DNA region upsteam of the MS45 promoter is SEQ ID NO: 9, the mutations of LS01 through LS15 are, respectively SEQ ID NOS: 10–24).

DISCLOSURE OF THE INVENTION

Figure 1:
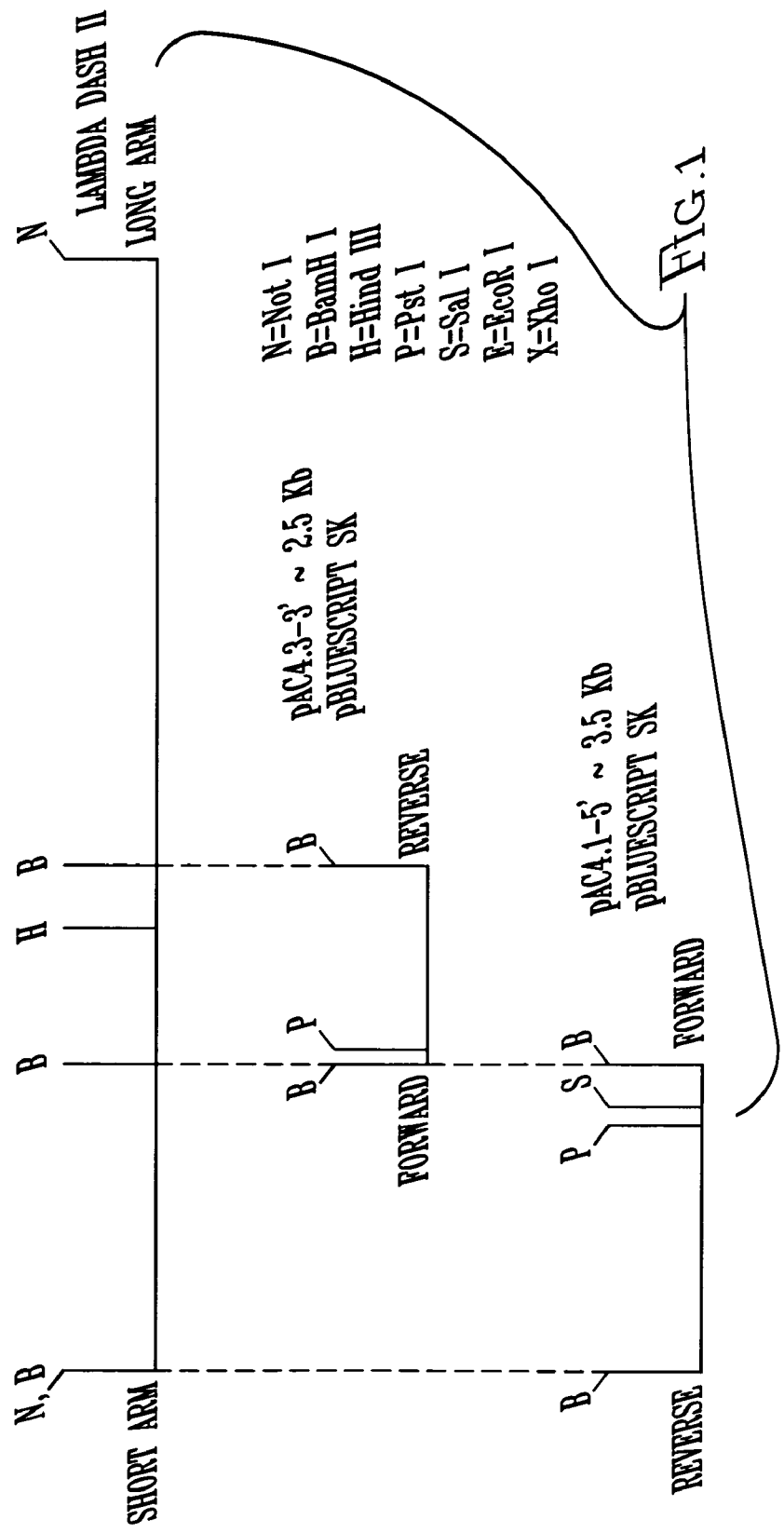
FIG. 1 is a diagram of Ac 4.1 Ms45 genomic clone and restriction sites.

All references referred to are incorporated herein by reference. Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, methods and examples are illustrative only and not limiting.

In the description that follows, a number of terms are used extensively. The following definitions are provided to facilitate understanding of the invention.

1. Definitions

Sequence identity or similarity, as known in the art, are relationships between two polypeptide sequences or two polynucleotide sequences, as determined by comparing the sequences. In the art, identity also means the degree of sequence relatedness between two polypeptide or two polynucleotide sequences as determined by the match between two strings of such sequences. Both identity and similarity can be readily calculated (*Computational Molecular Biology*; Lesk, A. M. ed.; Oxford University Press, New York; (1988); *Biocomputing: Informatics and Genome Projects*; Smith, D. W. ed.; Academic Press, New York; (1993); *Computer Analysis of Sequence Data* (Part I); Griffin, A. M. and H. G. Griffin eds.; Humana Press, New Jersey; (1994); von Heinje, G., *Sequence Analysis in Molecular Biology*; Academic Press; (1987); and *Sequence Analysis Primer*; Gribskov, M. and J. Devereux eds.; M Stockton Press, New York; (1991)). While there exist a number of methods to measure identity and similarity between two polynucleotide or two polypeptide sequences, both terms are well known to skilled artisans (von Heinje, G., *Sequence Analysis in Molecular Biology*; Academic Press; (1987); *Sequence Analysis Primer*; Gribskov, M. and J. Devereux eds.; M Stockton Press, New York; (1991); and Carillo, H., and D. Lipman, SIAM, *J. Applied Math.*; Vol. 48; pp. 1073; (1988)). Methods commonly employed to determine identity or similarity between two sequences include, but are not limited to those disclosed in Carillo, H., and D. Lipman, SIAM *J. Applied Math.*; Vol. 48; pp. 1073; (1988). Preferred methods to determine identity are designed to give the largest match between the two sequences tested. Methods to determine identity and similarity are codified in computer programs. Preferred computer program methods to determine identity and similarity between two sequences include, but are not limited to, GCG program package (Devereux, J., et al., *Nucleic Acids Research*; Vol. 12(1); pp. 387; (1984)), BLASTP, BLASTN, and FASTA (Atschul, S. F., et al., *J. Molec. Biol.*; Vol. 215; pp. 403; (1990)).

Male tissue consists of tissues made of collections of cells that are directly involved or supportive of the reproduction of the male gametes such as pollen, tapetum, anther, tassel, pollen mother cells and microspores. The tapetum is the tissue in the anther in closest contact with the pollen mother cells and microspores and is likely involved with the nutrition of the developing pollen grains. The pollen mother cells undergo two meiotic divisions to produce a tetrad of haploid microspores. Microspores undergo two mitoses to mature into a pollen grain. Pollen or pollen grains are mature male gametophytes that can have the ability to fertilize plants that are compatible. The anther is that portion of the stamen in which pollen is produced, the remainder of the stamen consisting of the filament, from which the anther depends. The stamen is the male organ of the flower.

The male tissue-preferred regulatory region is a nucleotide sequence that directs a higher level of transcription of an associated gene in male tissues than in some or all other tissues of a plant. For example, the Ms45 gene, described herein, is detected in anthers during quartet, quartet release and early uninucleate stages of development. For details regarding stages of anther development see Chang, M. T. and M. G. Neuffer, "Maize Microsporogenesis"; *Genome*; Vol. 32; pp. 232–244; (1989). The male tissue-preferred regulatory region of the Ms45 gene directs the expression of an operably linked gene in male tissues. The preferred tissues of expression are male, not for example, root or coleoptile tissue. Predominant expression is in male tissues such as, but not limited to, pollen, tapetum, anther, tassel, pollen mother cells and microspores. This male tissue-preferred expression refers to higher levels of expression in male tissues, but not necessarily to the exclusion of other tissues.

To mediate is to influence in a positive or negative way or to influence the outcome, such as with fertility or any other trait.

Male fertility is impacted when non-normal fertility is experienced; this can be as reduced fertility or increased fertility or fertility that is different in terms of timing or other characteristics.

Isolated means altered "by the hand of humans" from its natural state; i.e., that, if it occurs in nature, it has been changed or removed from its original environment, or both. For example, a naturally occurring polynucleotide or a polypeptide naturally present in a living organism in its natural state is not "isolated," but the same polynucleotide or polypeptide separated from the coexisting materials of its natural state is "isolated", as the term is employed herein. For example, with respect to polynucleotides, the term isolated means that it is separated from the chromosome and cell in which it naturally occurs. As part of or following isolation, such polynucleotides can be joined to other polynucleotides, such as DNAs, for mutagenesis, to form fusion proteins, and for propagation or expression in a host, for instance. The isolated polynucleotides, alone or joined to other polynucleotides such as vectors, can be introduced into host cells, in culture or in whole organisms. Introduced into host cells in culture or in whole organisms, such DNAs still would be isolated, as the term is used herein, because they would not be in their naturally occurring form or environment. Similarly, the polynucleotides and polypeptides may occur in a composition, such as media formulations, solutions for introduction of polynucleotides or polypeptides, for example, into cells, compositions or solutions for chemical or enzymatic reactions, for instance, which are not naturally occurring compositions, and, therein remain isolated polynucleotides or polypeptides within the meaning of that term as it is employed herein.

An exogenous gene refers in the present description to a DNA sequence that is introduced or reintroduced into an organism. For example, any gene, even the MS45 structural gene, is considered to be an exogenous gene, if the gene is introduced or reintroduced into the organism.

2. Isolation of a Male Tissue-Preferred Regulatory Region

Although anther-specific promoters and genes active in male tissues are known in the art, (McCormick, et al., "Anther-Specific Genes: Molecular Characterization and Promoter Analysis in Transgenic Plants," in *Plant Reproduction: From Floral Induction to Pollination*; Lord, et al. eds.; pp. 128–135; (1989); Scott, et al., International Application Publication No. WO 92/11379 (1992); van der Meer, et al., *The Plant Cell*; Vol. 4; pp. 253; (1992)), there are no generally accepted principles or structural criteria for recognizing DNA sequences that confer male tissue expression to gene expression in maize. Consequently, it is not possible to isolate a male tissue-preferred regulatory region directly from a maize genomic library by screening for a consensus sequence that confers male tissue-preferred expression.

For example, hybridization of such sequences may be carried out under conditions of reduced stringency, medium stringency or even highly stringent conditions (e.g., conditions represented by a wash stringency of 35–40% Formamide with 5× Denhardt's solution, 0.5% SDS and 1×SSPE at 37° C.; conditions represented by a wash stringency of 40–45% Formamide with 5× Denhardt's solution, 0.5% SDS and 1×SSPE at 42° C.; and conditions represented by a wash stringency of 50% Formamide with 5× Denhardt's solution, 0.5% SDS and 1×SSPE at 42° C., respectively). Medium stringency in a standard hybridization of nucleic acids would be useful in identifying the male tissue-preferred regulatory regions disclosed herein as well as other genes (see e.g. Sambrook, J., et al., *Molecular Cloning: a Laboratory Manual*; Cold Spring Harbor Laboratory Press, Cold Spring Harbor, N.Y.; (1982)). In general, sequences which code for a male tissue-preferred regulatory region will have sequence identity thereto of preferably 70%, 75%, or 80%, more preferably of 85%, or 90%, and most preferably of 95% or 99%.

Methods are readily available in the art for the hybridization of nucleic acid sequences. Hybridization screening of plated DNA libraries (see e.g. Sambrook, J., et al., *Molecular Cloning: a Laboratory Manual*; Cold Spring Harbor Laboratory Press, Cold Spring Harbor, N.Y.; (1982)) or amplifying coding sequences using the polymerase chain reaction (see e.g. Innis, et al., *PCR Protocols, a Guide to Methods and Applications*; Academic Press; (1990)) are well known techniques for isolating genomic DNA.

Regulatory regions may be identified in the genomic subclones using functional analysis, usually verified by the observation of reporter gene expression in anther tissue and the reduction or absence of reporter gene expression in non-anther tissue. This general approach is illustrated in Example 3, below. The possibility of the regulatory regions residing "upstream" or 5' ward of the transcriptional start site can be tested by subcloning a DNA fragment that contains the upstream region and subcloning small fragments into expression vectors for transient expression experiments. It is expected that smaller fragments may contain regions essential for male-tissue preferred expression. For example, the essential regions of the CaMV 19S and 35S promoters have been identified in relatively small fragments derived from larger genomic pieces as described in U.S. Pat. No. 5,352,605.

In general, sequences which code for a male tissue-preferred regulatory region will have sequence identity thereto of preferably 70%, 75%, or 80%, more preferably of 85%, or 90%, and most preferably of 95% or 99%.

Deletion analysis can occur from both the 5' and 3' ends of the regulatory region: fragments can be obtained by linker-scanning mutagenesis, mutagenesis using the polymerase chain reaction, and the like (*Directed Mutagenesis: A Practical Approach*; IRL Press; (1991)). The 3' deletions can delineate the male tissue-preferred regulatory region and identify the 3' end so that this essential region may then be operably linked to a core promoter of choice. Once the essential region is identified, transcription of an exogenous gene may be controlled by the male tissue-preferred region of Ms45 plus a core promoter. The core promoter can be any one of known core promoters such as a Cauliflower Mosaic Virus 35S or 19S promoter (U.S. Pat. No. 5,352,605), Ubiquitin (U.S. Pat. No. 5,510,474), the IN2 core promoter (U.S. Pat. No. 5,364,780), or a Figwort Mosaic Virus promoter (Gruber, et al., "Vectors for Plant Transformation" in *Methods in Plant Molecular Biology and Biotechnology*; Glick, et al. eds.; CRC Press; pp. 89–119; (1993)). Preferably, the promoter is the core promoter of a male tissue-preferred gene or the CaMV 35S core promoter. More preferably, the promoter is a promoter of a male tissue-preferred gene and in particular, the Ms45 core promoter.

Further mutational analysis can introduce modifications of functionality such as in the levels of expression, in the timing of expression or in the tissue of expression. Mutations may also be silent and have no observable effect.

3. Insertion of the Region into an Expression Vector

The selection of an appropriate expression vector with which to test for functional expression will depend upon the host and the method of introducing the expression vector into the host and such methods are well known to one skilled in the art. For eukaryotes, the regions in the vector include regions that control initiation of transcription and control processing. These regions are operably linked to a reporter gene such as the β-glucuronidase (GUS) gene or luciferase. General descriptions and examples of plant expression vectors and reporter genes can be found in Gruber, et al., "Vectors for Plant Transformation" in *Methods in Plant Molecular Biology and Biotechnology*; Glick, et al. eds; CRC Press; pp. 89–119; (1993). Gus expression vectors and Gus gene cassettes are commercially available from Clonetech, Palo Alto, Calif., while luciferase expression vectors and luciferase gene cassettes are available from Promega Corporation, Madison, Wis. Ti plasmids and other *Agrobacterium* vectors are described in Ishida, Y., et al., *Nature Biotechnology*; Vol. 14; pp. 745–750; (1996) and in U.S. Pat. No. 5,591,616 Method for Transforming Monocotyledons, filed May 3$^{rd}$, 1994.

Expression vectors containing putative regulatory regions located in genomic fragments can be introduced into intact tissues such as staged anthers, embryos or into callus. Methods of DNA delivery include microprojectile bombardment, DNA injection, electroporation and *Agrobacterium*-mediated gene transfer (see Gruber, et al., "Vectors for Plant Transformation," in *Methods in Plant Molecular Biology and Biotechnology*; Glick, et al. eds.; CRC Press; (1993), U.S. Pat. No. 5,591,616 Method for Transforming Monocotyledons, filed May 3$_{rd}$, 1994, and Ishida, Y., et al., *Nature Biotechnology*; Vol. 14; pp. 745–750; (1996)). General methods of culturing plant tissues are found in Gruber, et al., "Vectors for Plant Transformation," in *Methods in Plant Molecular Biology and Biotechnology*; Glick, et al. eds.; CRC Press; (1993).

For the transient assay system, staged, isolated anthers are immediately placed onto tassel culture medium (Pareddy, D. R. and J. F. Petelino, *Crop Sci. J.*; Vol. 29; pp. 1564–1566; (1989)) solidified with 0.5% Phytagel (Sigma, St. Louis) or other solidifying media. The expression vector DNA is introduced within 5 hours preferably by microprojectile-mediated delivery with 1.2 m particles at 1000–1100 Psi. After DNA delivery, the anthers are incubated at 26° C. upon the same tassel culture medium for 17 hours and analyzed by preparing a whole tissue homogenate and assaying for GUS or for luciferase activity (see Gruber, et al., "Vectors for Plant Transformation," in *Methods in Plant Molecular Biology and Biotechnology*; Glick, et al. eds.; CRC Press; (1993)).

The above-described methods have been used to identify DNA sequences that regulate gene expression in a male tissue-preferred manner. Such a region has been identified as the full length Ms45 male tissue-preferred regulatory region (SEQ ID No: 1). A TATA box mutation with sequence identity with the full length Ms45 male tissue-preferred regulatory region is identified in SEQ ID No: 2.

Thus, the present invention encompasses a DNA molecule having a nucleotide sequence of SEQ ID No: 1 (or those with sequence identity) and having the function of a male tissue-preferred regulatory region.

A putative TATA box can be identified by primer extension analysis as described in Example 2 below or in *Current Protocols in Molecular Biology*; Ausubel, F. M., et al., eds.; John Wiley and Sons, New York; pp. 4.8.1–4.8.5; (1987).

4. Use of a Male Tissue-Preferred Regulatory Region to Control Fertility

An object of the present invention is to provide a means to control fertility using a male tissue-preferred regulatory region. Importantly, this male tissue-preferred regulatory region can control the expression of an exogenous gene in anthers from quartet through early uninucleate stages of development. The practical significance of such timing is that the expression of a sterility-inducing gene during this developmental stage will disrupt anther maturation early enough to permit visual verification of the function of the sterility-inducing system in the field in that no anthers will be extruded. Thus, the effects of the sterility-inducing gene would be evident in the production field at a sufficiently early stage of development to allow either manual or mechanical detasseling of any "fertile escapes" that result from a partial or total breakdown of the sterility-inducing system.

One approach to control male fertility is to manipulate gene expression in the tapetum. The tapetum is a layer of cells that surrounds sporogenous cells in the anther and likely provides nutrients, such as reducing sugars, amino acids and lipids to the developing microspores (Reznickova, C. R., *Acad. Bulg. Sci.*; Vol. 31; pp. 1067; (1978); Nave, et al., *J. Plant Physiol.*; Vol. 125; pp. 451; (1986); Sawhney, et al., *J. Plant Physiol.*; Vol. 125; pp. 467; (1986)). Ms45 is found to be highly expressed in the tapetal layer. Tapetal cells also produce β(1,3)-glucanase ("callase") which promotes microspore release (Mepham, et al., *Protoplasma*; Vol. 70; pp. 1; (1970)). Therefore, a delicate relationship exists between the tapetum and the sporogenous cells, and any disruption of tapetal function is likely to result in dysfunctional pollen grains. In fact, lesions in tapetal biogenesis are known to result in male sterility mutants (Kaul, "Male Sterility in Higher Plants" in *Monographs on Theoretical and Applied Genetics*; Frankel et al. eds.; Springer Verlag; Vol. 10; pp. 15–95; (1988)). A premature or late appearance of callase during the development of the tapetum is also associated with certain types of male sterility (Warmke, et al., *J. Hered.*; Vol. 63; pp. 103; (1972)). Therefore, the callase gene can be used to disrupt male tissue function. Scott, et al., PCT WO 93/02197 (1993), discloses the nucleotide sequence of a tapetum-specific callase. Thus, a failure of the microspores to develop into mature pollen grains can be induced using a recombinant DNA molecule that comprises a gene capable of disrupting tapetal function under the control of tapetum-specific regulatory sequences.

One general approach to impact male fertility is to construct an expression vector in which the male tissue-preferred regulatory region is operably linked to a nucleotide sequence that encodes a protein capable of disrupting male tissue function, resulting in infertility. Proteins capable of disrupting male tissue function include proteins that inhibit the synthesis of macromolecules that are essential for cellular function, enzymes that degrade macromolecules that are essential for cellular function, proteins that alter the biosynthesis or metabolism of plant hormones, structural proteins, inappropriately expressed proteins and proteins that inhibit a specific function of male tissues.

For example, an expression vector can be constructed in which the male tissue-preferred regulatory region is operably linked to a nucleotide sequence that encodes an inhibitor of protein synthesis, which could be but is not limited to a cytotoxin. Diphtheria toxin, for example, is a well-known inhibitor of protein synthesis in eukaryotes. DNA molecules encoding the diphtheria toxin gene can be obtained from the American Type Culture Collection (Rockville, Md.), ATCC No. 39359 or ATCC No. 67011 and see Fabijanski, et al., E.P. Appl. No. 90902754.2, "Molecular Methods of Hybrid Seed Production" for examples and methods of use. DAM methylase, for example, is a well known enzyme from *Escherichia coli* which modifies the adenine residue in the sequence 5' GATC 3' to $N^6$-methyl-adenine. Cigan and Albertsen describe how DAM methylase could be used to impact fertility in transgenic plants (PCT/US95/15229 Cigan, A. M. and Albertsen, M. C., "Reversible Nuclear Genetic System for Male Sterility in Transgenic Plants"). Another example of a protein which disrupts fertility is avidin as illustrated in U.S. patent application Ser. No. 08/475,582 "Induction of Male Sterility in Plants by Expression of High Levels of Avidin" by Howard, J. and Albertsen, M. C.

Alternatively, the disruption of tapetal function can be achieved using DNA sequences that encode enzymes capable of degrading a biologically important macromolecule. For example, Mariani, et al., *Nature*; Vol. 347; pp. 737; (1990), have shown that expression in the tapetum of either *Aspergillus oryzae* RNase-T1 or an RNase of *Bacillus amyloliquefaciens*, designated "bamase," induced destruction of the tapetal cells, resulting in male infertility. Quaas, et al., *Eur. J. Biochem.*; Vol. 173; pp. 617; (1988), describe the chemical synthesis of the RNase-T1, while the nucleotide sequence of the bamase gene is disclosed in Hartley, *J. Molec. Biol.*; Vol. 202; pp. 913; (1988).

RNase-T1 and bamase genes may be obtained, for example, by synthesizing the genes with mutually priming long oligonucleotides. See, for example, *Current Protocols in Molecular Biology*; Ausubel, F. M., et al., eds.; John Wiley and Sons, New York; pp. 8.2.8 to 8.2.13; (1987). Also, see Wosnick, et al., *Gene*; Vol. 60; pp. 115; (1987). Moreover, current techniques using the polymerase chain reaction provide the ability to synthesize very large genes (Adang, et al., *Plant Molec. Biol.*; Vol. 21; pp. 1131; (1993); Bambot, et al., *PCR Methods and Applications*; Vol. 2; pp. 266; (1993)).

In an alternative approach, pollen production is inhibited by altering the metabolism of plant hormones, such as auxins. For example, the rolB gene of *Agrobacterium rhizogenes* codes for an enzyme that interferes with auxin metabolism by catalyzing the release of free indoles from indoxyl-β-glucosides. Estruch, et al., *EMBO J.*; Vol. 11; pp. 3125; (1991) and Spena, et al., *Theor. Appl. Genet.*; Vol. 84; pp. 520; (1992), have shown that the anther-specific expression of the rolB gene in tobacco resulted in plants having shriveled anthers in which pollen production was severely decreased. Therefore, the rolB gene is an example of a gene that is usefull for the control of pollen production. Slightom, et al., *J. Biol. Chem.*; Vol. 261; pp. 108; (1985), disclose the nucleotide sequence of the rolB gene.

In order to express a protein that disrupts male tissue function, an expression vector is constructed in which a DNA sequence encoding the protein is operably linked to DNA sequences that regulate gene transcription in a male tissue-preferred manner. The general requirements of an expression vector are described above in the context of a transient expression system. Here, however, the preferred mode is to introduce the expression vector into plant embryonic tissue in such a manner that an exogenous protein will be expressed at a later stage of development in the male tissues of the adult plant. Mitotic stability can be achieved using plant viral vectors that provide epichromosomal replication.

An alternative and preferred method of obtaining mitotic stability is provided by the integration of expression vector sequences into the host chromosome. Such mitotic stability can be provided by the microprojectile delivery of an expression vector to embryonic tissue (Gruber, et al., "Vectors for Plant Transformation," in *Methods in Plant Molecular Biology and Biotechnology*; Glick, et al. eds.; CRC Press; (1993)).

Transformation methodology can be found for many plants, including but not limited to sunflower, soybean, wheat, canola, rice and sorghum (Knittel, N., et al., *J. Plant Cell Rep.*; Springer International, Berlin, W. Germany; Vol. 14(2/3); pp. 81–86; (1994); Chee, P. P., et al., *Plant Physiol.*; American Society of Plant Physiologists, Rockville, Md.; Vol. 91(3); pp. 1212–1218; (1989); Hadi, M. Z., et al., *J. Plant Cell Rep.*; Springer International, Berlin, W. Germany; Vol. 15(7); pp. 500–505; (1996); Perl, A., et al., *Molecular and General Genetics*; Vol. 235(2–3); pp. 279–284; Zaghmout, O. M. F. and N. L. Trolinder, *Nucleic Acids Res*; IRL Press, Oxford; Vol. 21(4); pp.1048; (1993); Chen, J. L. and W. D. Beversdorf, *Theor. Appl. Genet.*; Springer International, Berlin, W. Germany; Vol. 88(2); pp.187–192; (1994); Sivamani, E., et al., *Plant Cell Rep.*; Springer International, Berlin, W. Germany; Vol. 15(5); pp. 322–327; (1996); Hagio, T., et al., *Plant Cell Rep.*; Vol. 10(5); pp. 260–264; (1991)) and are also known to those skilled in the art.

In order to select transformed cells, the expression vector contains a selectable marker gene, such as a herbicide resistance gene. For example, such genes may confer resistance to phosphinothricine, glyphosate, sulfonylureas, atrazine, imidazolinone or kanamycin. Although the expression vector can contain cDNA sequences encoding an exogenous protein under the control of a male tissue-preferred regulatory region, as well as the selectable marker gene under control of constitutive promoter, the selectable marker gene can also be delivered to host cells in a separate selection expression vector. Such a "co-transformation" of embryonic tissue with a test expression vector containing a male tissue-preferred regulatory region and a selection expression vector is illustrated below.

5. Induction of Sterility

In an alternative approach, male sterility can be induced by the use of an expression vector in which the male tissue-preferred regulatory region is operably linked to a nucleotide sequence that encodes a complementary nucleotidic unit. The binding of complementary nucleic acid molecules to a target molecule can be selected to be inhibitory. For example, if the target is an mRNA molecule, then binding of a complementary nucleotide unit, in this case an RNA, results in hybridization and in arrest of translation (Paterson, et al., *Proc. Nat'l. Acad. Sci.*; Vol. 74; pp. 4370; (1987)). Thus, a suitable antisense RNA molecule, such as one complementary to Ms45 (U.S. Pat. No. 5,478,369), would have a sequence that is complementary to that of an mRNA species encoding a protein that is necessary for male sterility (Fabijanski in "Antisense Gene Systems of Pollination Control For Hybrid Seed Production", U.S. Pat. App. No. 08/288,734).

For example, the production of callase antisense RNA would inhibit the production of the callase enzyme which is essential for microspore release. In addition, male sterility can be induced by the inhibition of flavonoid biosynthesis using an expression vector that produces antisense RNA for the 3' untranslated region of chalcone synthase A gene (Van der Meer, et al., *The Plant Cell*; Vol. 4; pp. 253; (1992)). The cloning and characterization of the chalcone synthase A gene is disclosed by Koes, et al., *Gene*; Vol. 81; pp. 245; (1989), and by Koes, et al., *Plant Molec. Biol.*; Vol. 12; pp. 213; (1989).

Alternatively, an expression vector can be constructed in which the male tissue-preferred regulatory region is operably linked to a nucleotide sequence that encodes a ribozyme. Ribozymes can be designed to express endonuclease activity that is directed to a certain target sequence in an mRNA molecule. For example, Steinecke, et al., *EMBO J.*; Vol. 11; pp. 1525; (1992), achieved up to 100% inhibition of neomycin phosphotransferase gene expression by ribozymes in tobacco protoplasts. More recently, Perriman, et al., *Antisense Research and Development*; Vol. 3; pp. 253; (1993), inhibited chloramphenicol acetyl transferase activity in tobacco protoplasts using a vector that expressed a modified hammerhead ribozyme. In the context of the present invention, appropriate target RNA molecules for ribozymes include mRNA species that encode proteins essential for male fertility, such as callase mRNA and Ms45 mRNA.

In a further alternative approach, expression vectors can be constructed in which a male tissue-preferred regulatory region directs the production of RNA transcripts capable of promoting RNase P-mediated cleavage of target mRNA molecules. According to this approach, an external guide sequence can be constructed for directing the endogenous ribozyme, RNase P, to a particular species of intracellular mRNA, which is subsequently cleaved by the cellular ribozyme (U.S. Pat. No. 5,168,053; Yuan, et al., *Science*; Vol. 263; pp. 1269; (1994)). Preferably, the external guide sequence comprises a ten to fifteen nucleotide sequence complementary to an mRNA species that encodes a protein essential for male fertility, and a 3'-RCCA nucleotide sequence, wherein R is preferably a purine. The external guide sequence transcripts bind to the targeted mRNA species by the formation of base pairs between the mRNA and the complementary external guide sequences, thus promoting cleavage of mRNA by RNase P at the nucleotide located at the 5'-side of the base-paired region.

Another alternative approach is to utilize aptamer technology, where the complementary nucleotidic unit is a nucleotide that serves as a ligand to a specified target molecule (U.S. Pat. No. 5472841). This target could be a product essential for male fertility or a product disrupting male fertility. Using this method, an aptamer could be selected for the target molecule, Ms45 or avidin for example, that would bind and inhibit expression of the target. The nucleotide sequence encoding the aptamer would be part of expression vectors constructed so that a male tissue-preferred regulatory region directs the production of the aptamer.

Sterility can also be induced by interruption of a gene important in male fertility such as the Ms45 or the Ms2 gene (Mark, G. M., et al., *Nature*; Vol. 363; pp. 715–717; (1993)). Methods of gene interruption are well known in the art and include, but are not limited to, transposable element insertion and mutation induction.

6. Restoration of Male Fertility in the F1 Hybrid

The above-described methods can be used to produce transgenic male-sterile maize plants for the production of F1 hybrids in large-scale directed crosses between inbred lines. If the egg cells of the transgenic male-sterile plants do not all contain the exogenous gene that disrupts tapetal function, then a proportion of F1 hybrids will have a male-fertile phenotype. On the other hand, F1 hybrids will have a male-sterile phenotype if the exogenous gene is present in all egg cells of the transgenic male-sterile plants because sterility induced by the exogenous gene would be dominant. Thus, it is desirable to use a male fertility restoration system to provide for the production of male-fertile F1 hybrids. Such a fertility restoration system has particular value when the harvested product is seed or when crops are self-pollinating.

Also, such a fertility restoration system has particular value when the male tissue-preferred regulatory region is operatively linked to an inducible promoter such as in WO 89/10396 (Marianai, et al., *Plants with Modified Stamen Cells*) and the inducible promoter is responsive to external controls. This linked male tissue-preferred regulatory region consists of a male tissue-preferred regulatory region, an inducible promoter and an exogenous gene.

One approach to male fertility restoration would be to cross transgenic male-sterile plants with transgenic male-fertile plants which contain a fertility restoration gene under the control of a male tissue-preferred regulatory region. For example, Fabijanski in "Antisense Gene Systems of Pollination Control For Hybrid Seed Production", U.S. patent application Ser. No. 08/288,734, crossed male-fertile plants that expressed a barnase inhibitor, designated "barstar," with male-sterile plants that expressed barnase. Hartley, *J. Mol. Biol.*; Vol. 202; pp. 913; (1988), discloses the nucleotide sequence of barstar.

Another approach would be to cross male-sterile plants containing a disruption in an essential male fertility gene, to transgenic male fertile plants containing the male tissue-preferred regulatory region operably linked to a non-disrupted copy of the fertility gene such as Ms45 or Ms2 gene.

The full sequence of the Ms45 gene is contained in U.S. Pat. No. 5,478,369 and Ms2 in Mark, G. M., et al., *Nature*; Vol. 363; pp. 715–717; (1993).

Alternatively, male fertility restoration can be achieved by expressing complementary nucleotidic units such as toxin expressing ribozymes or aptamers in male-fertile plants to neutralize the effects of toxin in male-sterile plants. Thus, male fertility can be restored in the F1 hybrids by producing a male-fertile transgenic plant that synthesizes a particular species of RNA molecule or polypeptide to counteract the effects of the particular exogenous gene expressed in the male-sterile transgenic plants.

In an alternative method for restoring male fertility, transgenic male-sterile plants contain an expression vector having a male tissue-preferred regulatory region, a prokaryotic regulatory region (from a prokaryotic regulatory system), and an exogenous gene that is capable of disrupting tapetal function. Transgenic male-fertile plants are produced that express a prokaryotic peptide under the control of a male tissue-preferred regulatory region. In the resulting F1 hybrids from the male-sterile and male-fertile cross, the prokaryotic peptide binds to the prokaryotic regulatory sequence and represses the expression of the exogenous gene which is capable of disrupting male fertility. An advantage of this method of fertility restoration is that one form of transgenic male-fertile plant can be used to provide F1 fertility regardless of the identity of the exogenous gene that was used to disrupt tapetal function in the transgenic male-sterile plant.

For example, the LexA gene/LexA operator system can be used to regulate gene expression pursuant to the present invention. See U.S. Pat. No. 4,833,080 and Wang, et al., *Mol. Cell. Biol.*; Vol. 13; pp. 1805; (1993). More specifically, the expression vector of the male-sterile plant would contain the LexA operator sequence, while the expression vector of the male-fertile plant would contain the coding sequences of the LexA repressor. In the F1 hybrid, the LexA repressor would bind to the LexA operator sequence and inhibit transcription of the exogenous gene that encodes a product capable of disrupting male fertility. These would include, but are not limited to, avidin, DAM methylase, diptheria toxin, RNase T, bamase, rol B and chalcone synthase A.

LexA operator DNA molecules can be obtained, for example, by synthesizing DNA fragments that contain the well-known LexA operator sequence. See, for example, U.S. Pat. No. 4,833,080 and Garriga, et al., *Mol. Gen. Genet.*; Vol. 236; pp. 125; (1992). The LexA gene may be obtained by synthesizing a DNA molecule encoding the LexA repressor. Gene synthesis techniques are discussed above and LexA gene sequences are described, for example, by Garriga, et al., *Mol. Gen. Genet.*; Vol. 236; pp. 125; (1992). Alternatively, DNA molecules encoding the LexA repressor may be obtained from plasmid pRB500, American Type Culture Collection accession No. 67758. Those of skill in the art can readily devise other male fertility restoration strategies using prokaryotic regulatory systems, such as the lac repressor/lac operon system or the trp repressor/trp operon system.

7. Identification of Essential Parts of Regulatory Region

Identification of the essential parts of a regulatory region can be performed by deleting, adding and/or substituting nucleotides in a regulatory region by methods well known to one skilled in the art. Such variants can be obtained, for example, by oligonucleotide-directed mutagenesis, linker-scanning mutagenesis and mutagenesis using the polymerase chain reaction (*Directed Mutagenesis: A Practical Approach*; IRL Press; (1991)).

A series of 5' deletions of a regulatory region can be constructed using existing restriction sites. The resulting promoter fragments can be tested for activity using an expression vector as previously discussed. Further refinement and delineation may be obtained by making smaller changes, preferably of about 50 or 30 nucleotides, more preferably of about 20 or 10 nucleotides and most preferably of about 5 or 1 nucleotides, to the smallest restriction fragment that still confers proper expression upon the reporter construct (*Directed Mutagenesis: A Practical Approach*; IRL Press; (1991)). These can be introduced into the expression vector using introduced or natural restriction sites. A series of 3' deletions can also be generated as discussed above or by PCR or by methods well known to one skilled in the art (*Directed Mutagenesis: A Practical Approach*; IRL Press; (1991)). Further refinement and delineation may be obtained by making smaller changes, preferably of about 50 or 30 nucleotides, more preferably of about 20 or 10 nucleotides and most preferably of about 5 or 1 nucleotides, to the smallest restriction fragment that still confers proper expression upon the reporter construct (*Directed Mutagenesis: A Practical Approach*; IRL Press; (1991)).

These 5' and 3' deletions therefore will delineate the minimal region essential for mimicking the proper tissue and temporal expression of the longer regulatory region. In general, sequences which code for this minimal region of a male tissue-preferred regulatory region will have sequence identity thereto preferably of about 70%, 75%, or 80%, more preferably of about 85%, or 90%, and most preferably of about 95% or 99%.

Deletional analysis has demonstrated that the functional sequences are located in the −38 to −195 region upstream of the TATA box. Important regions in that area include the −72 to −121 region and −142 to −171 region. An essential region is −72 to −111.

The following is presented by way of illustration and is not intended to limit the scope of the invention.

EXAMPLE 1

Genomic Cloning and Sequencing of Ms45 Promoter

The Ac tagging and identification of the Ms45 cDNA and Northern analysis is described in U.S. Pat. No. 5,478,369.

A partial cDNA of Ms45 was used to screen a B73 maize genomic library. This library was made by cloning SAU3A1 partials into a BAMHI digested genomic cloning vector (Lambda Dash II, Stratagene, La Jolla, Calif.). Approximately $1 \times 10^6$ plaques were screened using an *E. coli* strain suitable for genomic DNA (ER1647, New England Biolabs, MA) as the host. Clone AC4.1 was purified to homogeneity after three rounds of screening. Restriction mapping of AC4.1 showed the clone to be about 13 kb in length and contained two internal BAMHI sites (FIG. 1). One of these sites was also found in the Ms45 partial cDNA. Two BAMHI fragments were subcloned to a cloning vector (Bluescript SK+, Stratagene, La Jolla, Calif.). The 5' end clone was about 3.5 kb in length and corresponded to sequence upstream (5') of the internal BAMHI site. The 3' end clone was 2.5 kb and contained Ms45 sequence downstream of the internal BAMHI site. Concurrently, a putative full length Ms45 cDNA was isolated and sequenced. By sequence comparison of the 5' end clone and the Ms45 cDNA the putative translational start site was identified (FIG. 1).

Sequencing of the Ms45 promoter region was accomplished using the dideoxy chain termination method of Sanger, F., et al., "DNA Sequencing with Chain Terminating Inhibitors"; *Proc. Nat'l. Acad. Sci.*; Vol. 74; pp. 5463–5467; (1977). Genomic clone pac4.1–5' (FIG. 1) was sequenced using the universal oligo and others that were sequence specific using techniques well known in the art.

Figure 2:
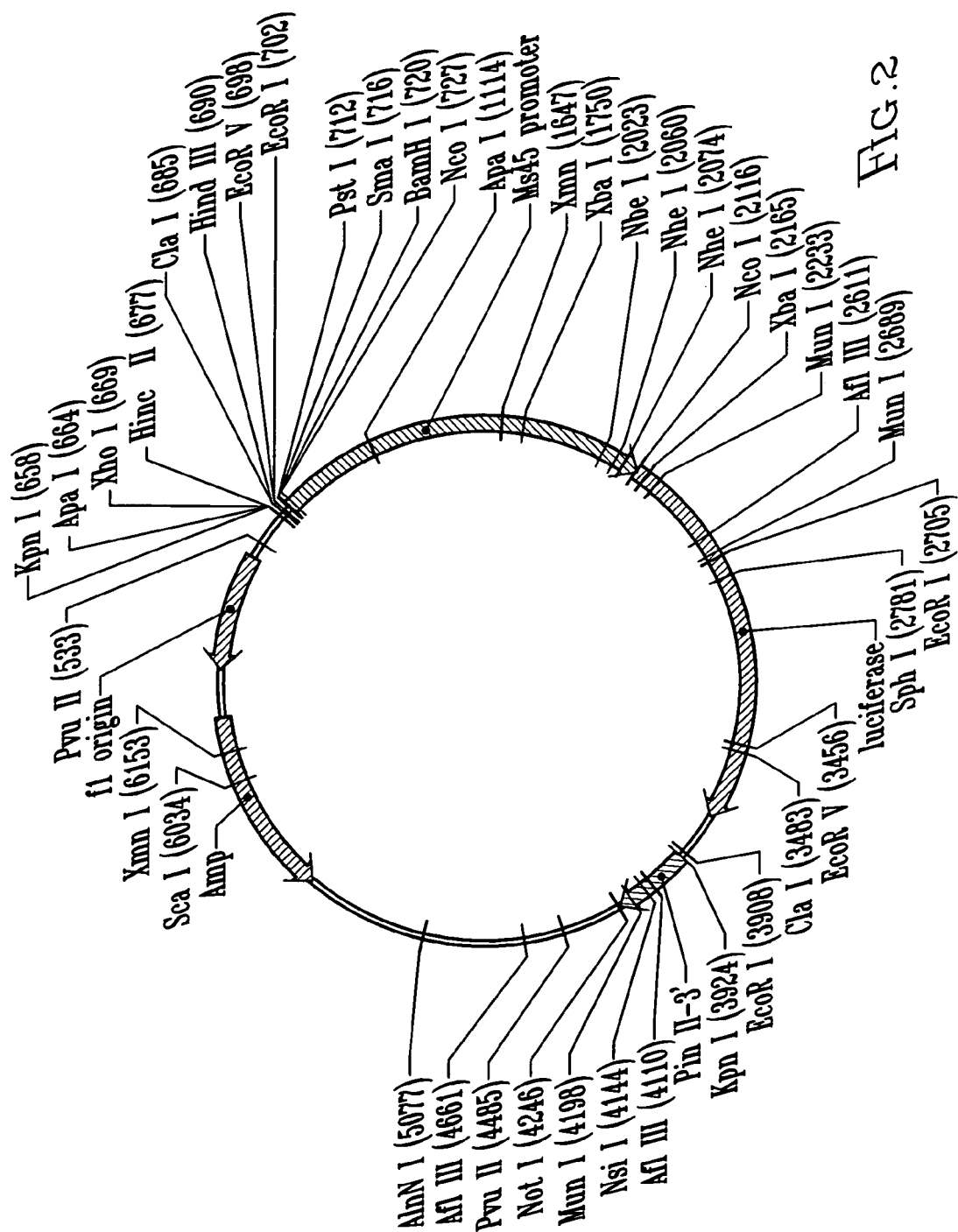
FIG. 2 is a plasmid map of PHP6045.

The male tissue-preferred regulatory region had an NCOI site introduced at the start codon and was cloned as an NCOI fragment into a promoterless Luci expression vector. This new reporter vector was designated as plasmid PHP6045 (FIG. 2) ATCC No: 97828 (Deposited Dec. 12, 1996; American Type Culture Collection, 12301 Parklawn Dr., Rockville, Md. 20852).

EXAMPLE 2

Primer Extension Analysis

Total RNA was isolated from maize tassels containing quartet through early uninucleate stage anthers. The total RNA was precipitated with ethanol and $MgCl_2$. One milligram of total RNA was isolated and the poly A+ mRNA was purified by using oligo-dT cellulose. Poly A+ RNA was also isolated directly from 6 day old maize seedling leaves and maize anthers using protocols known to those skilled in the art.

A sequencing ladder was prepared using a single. stranded Ms45 oligonucleotide and incorporation of 35S-dATP in a standard sequencing procedure, using protocols well known to one skilled in the art.

Primer Extension was Done According to the Method Below:

I. 5'-end labeling Synthetic Oligonucleotide Primer.
    Combined: 5 pmol primer N1 1916 (PHL11916) inl.1.0 μl
    5 μl(50 μCi) gamma 32P-ATP (>5000 Ci/mmole)
    0.7 μl 10× kinase buffer
    0.7 μl T4 polynucleotide kinase incubated 37° C., 45 min Diluted with 20 μl TE and heated to 65° C. to inactivate enzyme.

| 10X Kinase Buffer | To make 1 ml |
|---|---|
| 0.5 M Tris-HCl, pH 7.6–8.0 | 0.5 ml of 1 M |
| 5 mM spermidine | 0.05 ml of 0.1 M |
| 100 mM MgCl2 | 0.1 ml of 1 M |
| 100 mM DTT | 0.5 ml of 0.5 M |
| 0.1 mg/ml gelatin or BSA | 50 μl of 2 mg/ml |
| | 0.1 ml water |

II. Annealed Primer and RNA

Kinased primers were annealed to mRNA from maize tassel, 6d maize seedling leaves, maize anthers and 6d maize leaves. Mixed together on ice were 2 μl mRNA, 1 μl kinased oligo, 2 μl 5× annealing buffer (1.25M KCl, 10 mM Tris, pH 7.9–8.15), and 1 μl 30 mM vanadyl. The total volume was brought to 10 μl with 10 mM Tris, pH 8.15. This mixture was heated to 65° C. and cooled to 55° C. for 4 hours period on thermocycler heating block.

III. Primer Extension

23 μl primer extension mix (see recipe below) and 0.4 μl reverse transcriptase (SuperScript, BRL, MD) were added to each tube. This was mixed by gently pipeting up and down and placed immediately in 48° C. and incubated 45 min. Primer Extension Mix consists of 10 mM MgCl2, 5 mM DTT, 0.33 mM each dATP, dCTP, dGTP, dTTP and DEPC water.

Figure 3:
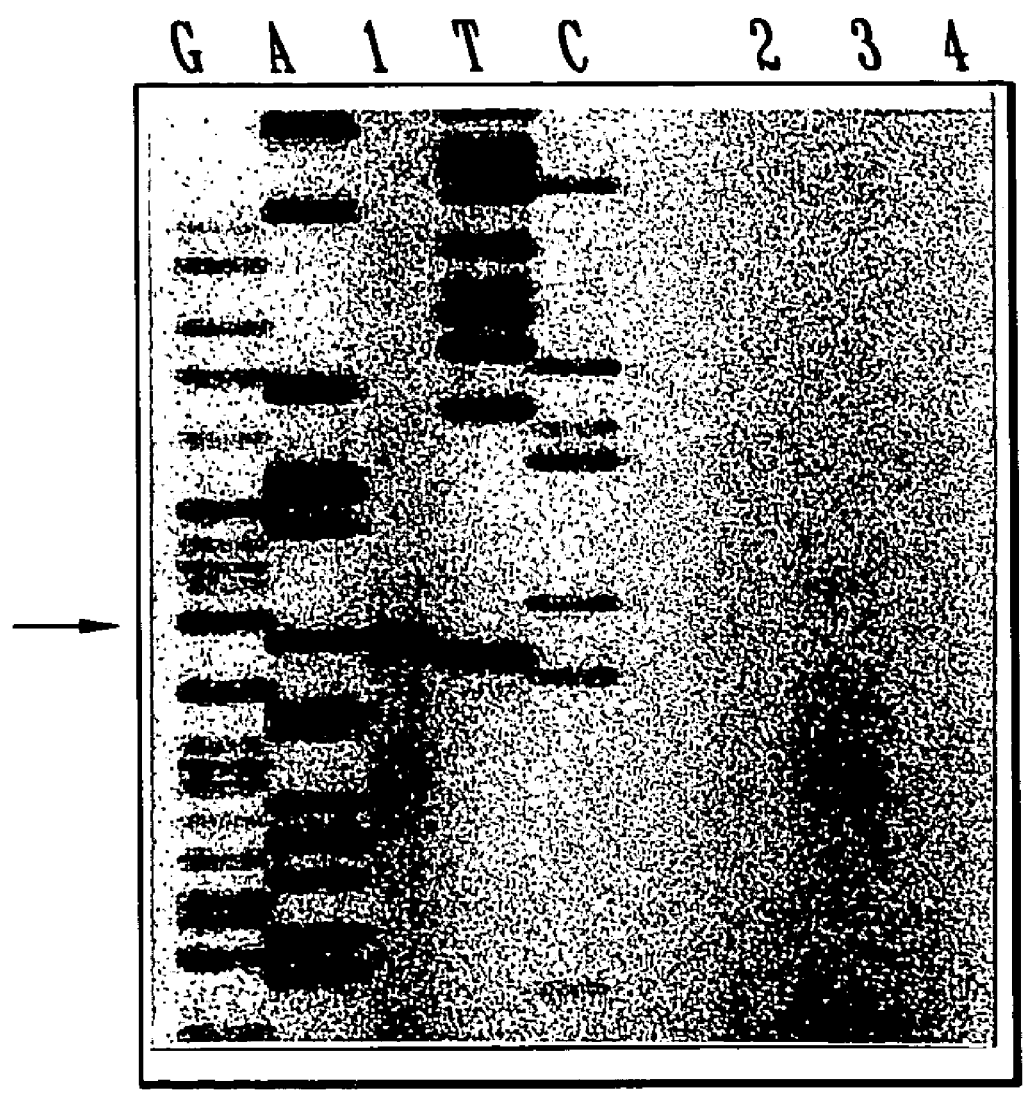
FIG. 3 is an autoradiogram of the primer extension products indicating the start of transcription of Ms45. Lanes labeled G, A, T, C, correspond to sequencing reactions with dideoxynucleotides ddGTP, ddATP, ddTTP, and ddCTP, respectively. Lanes 1–4 correspond to primer extension reactions with mRNA from (1) tassels, (2) leaves, (3) anthers, and (4) leaves.

300 μl ethanol was added and precipitated in −20° C. freezer overnight, then pelleted 30 minutes in a microfuge. Pellets were dried in a Speed Vac and dissolved in 6 μl of 0.1 NaOH/1 mM EDTA. Tube contents were mixed by pipetting and vortexing to insure that pellets were dissolved. These were left at room temp 2.5 hours, and 6 μl sequencing dye (Stop solution from USB Sequencing kit) was added, and the solution was denatured at approximately 95° C. One half of the sample was loaded on 6% denaturing polyacrylamide sequencing gel with stacking buffer and run at 55 Watts for 2 hours. The gel was dried in a gel dryer and exposed to Kodak X-AR film. After a three day exposure, a transcription product was observed in the maize tassel mRNA primer extension reaction which corresponded to a deoxythymidine located 42 nucleotides upstream of the start codon (FIG. 3). This position was designated as +1. A minor start of transcription was also identified at −3.

EXAMPLE 3

Figure 5:
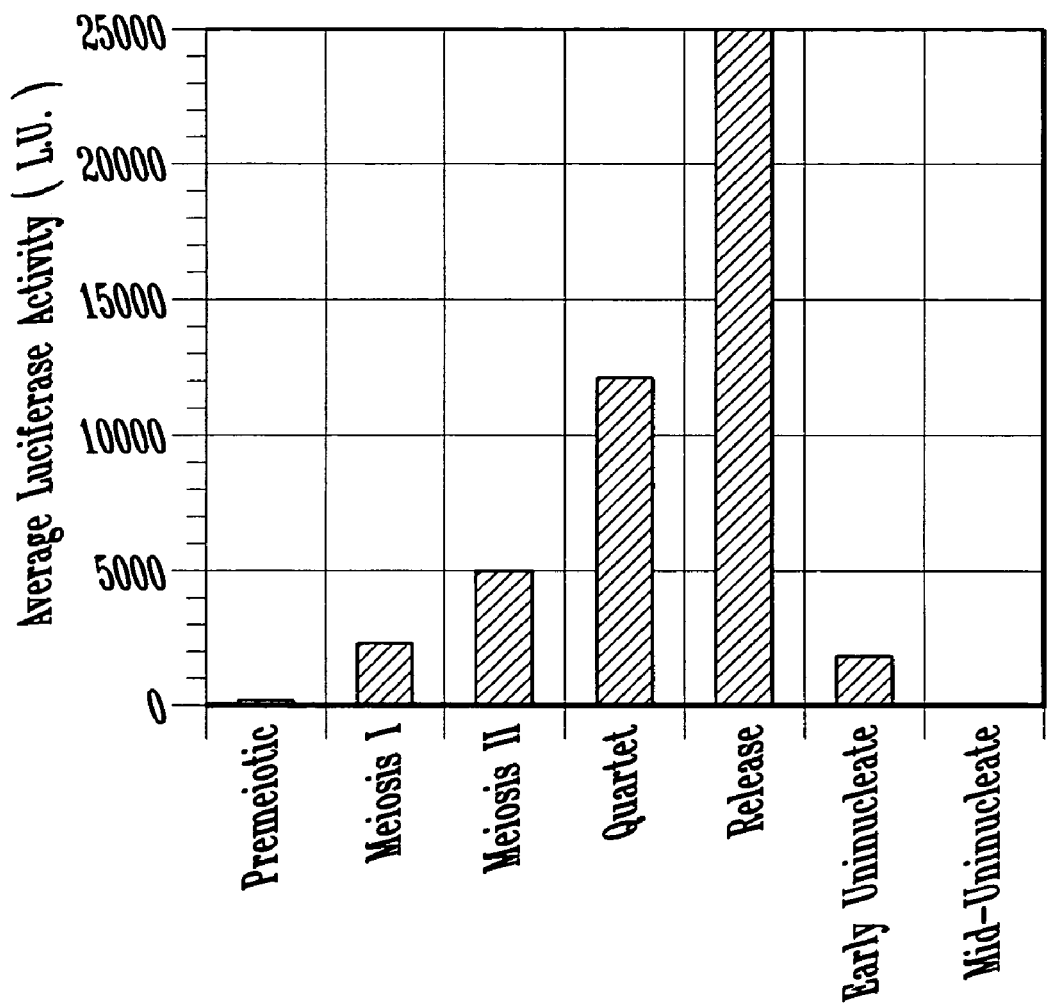
FIG. 5 is a bar graph illustrating the stage specificity of the Ms45 Male Tissue-Preferred Regulatory Region.

Determination of Stage and Tissue Specificity of the Ms45 Male Tissue-Preferred Regulatory Region The full-length male tissue-preferred regulatory region (SEQ ID No: 1) was fused to the luciferase reporter gene from the firefly, *Photinus pyralis*, (DeWit, T. R., et al., *Proc. Nat'l Acad. Sci. USA*; Vol. 82; pp. 7870–7873; (1985)) with the PinII-3' nontranslated region from potato (An, G., et al., "Functional Analysis of the Control Region of the Potato Wound-Inducible Proteinase Inhibitor II Gene"; *Plant Cell*; Vol. 1; pp. 115–122; (1989)). Maize anthers at various stages of development were plated on tassel culture medium (Pareddy, et al., *Theoret. Appl. Genet.*; Vol. 77; pp. 521–526; (1989)), solidified with agar (Phytagar®, Sigma, St. Louis). One of the three anthers from each floret was staged, and the remaining anthers were pooled by stage and plated for microprojectile bombardment, typically eight anthers per plate. The anthers were shot at 1100 p.s.i. with 1.8 m tungsten particles onto which was precipitated DNA of the Ms45 male tissue-preferred regulatory region- luciferase reporter construct. All anthers on a given plate were at the same stage: premeiotic, meiosis I, meiosis II, quartet, microspore release, early uninucleate microspore, or mid-uninucleate microspore. Three repetitions were shot of each stage. Anthers were incubated overnight at 26° C. for 18 hr. A crude extract was prepared with the anthers from each plate and assayed for luciferase activity and protein content. The luciferase activity, normalized to protein concentration, is graphed in FIG. 5 as a function of stage of development. The major activity was at the quartet and microspore release stages of development, with minor activity in meiosis I and II, and barely detectable activity in the early uninucleate stage. No significant activity above background was detected in premeiotic or mid-uninucleate anthers.

Figure 6A:
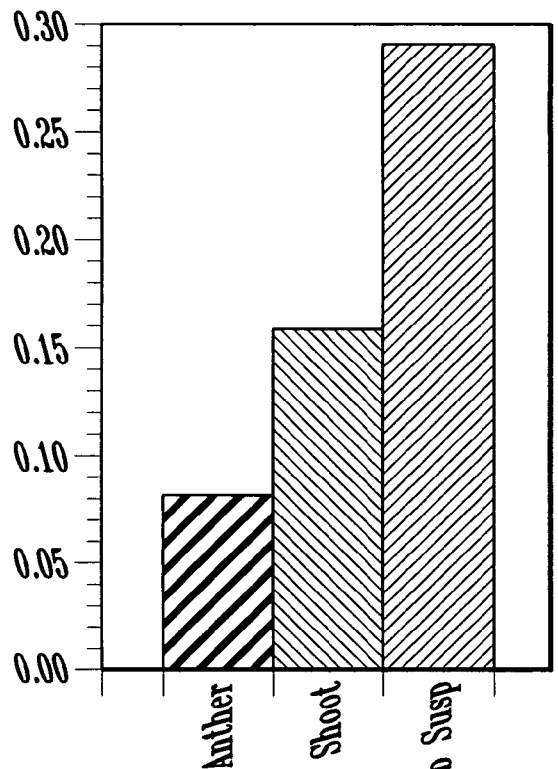
FIG. 6 illustrates tissue specificity illustrated by lack of activity in non-male tissue the ubiquitin regulatory region was active in non-male tissues (FIG. 6A), but the Ms45 male tissue-preferred regulatory region was not.
Figure 6B:
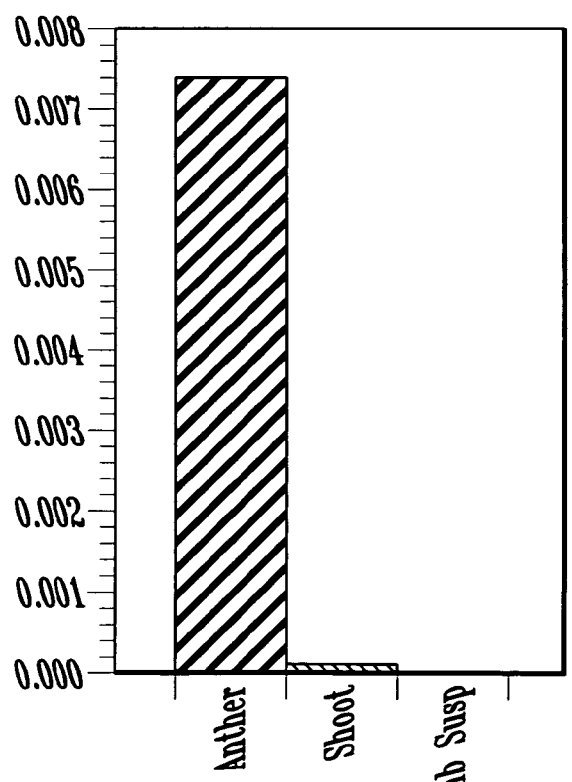

In addition, embryogenic callus, cultured on MS medium containing 2.0 ug/ml of 2,4-D was bombarded in the same manner, except at 650 p.s.i. with particles coated with a luciferase reporter fused either to the Ms45 male tissue-preferred regulatory region or to a maize ubiquitin promoter (U.S. Pat. No. 5,510,474) and a uidA (GUS) reporter fused to a maize ubiquitin promoter. Luciferase was normalized to β-glucuronidase. As shown in FIG. 6, the Ms45 male tissue-preferred regulatory region was incapable of driving transient expression in embryogenic callus and shoots, even though the ubiquitin promoter was expressed. Similarly, maize seeds, imbibed and germinated in distilled water for two days and placed on wet filters, were subjected to microprojectile bombardment and their hypocotyls assayed for luciferase and β-glucuronidase. The ubiquitin regulatory region (promoter) was active, but the Ms45 male tissue-preferred regulatory region was not.

Figure 4:
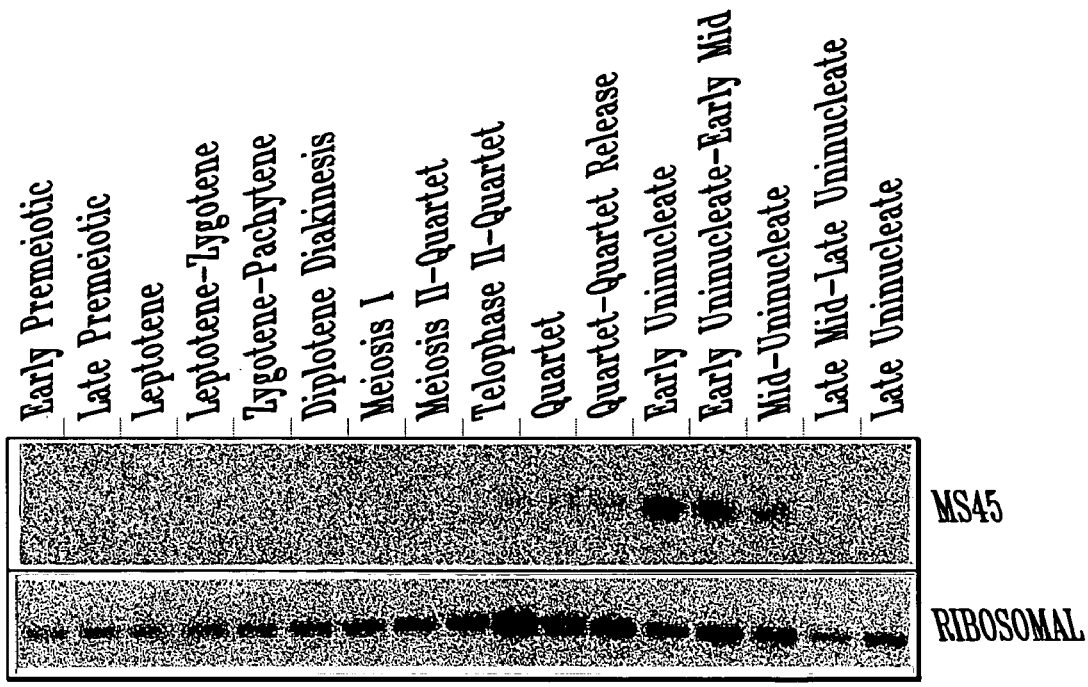
FIG. 4 shows an anther mRNA Northern analysis gel hybridized with the male fertility gene Ms45.

This result is paralleled by the results of RNA hybridization analysis. Maize anthers at various stages of development were collected and treated as follows. One of the three anthers from each floret was fixed in (3:1 ethanol: glacial acetic acid) in a well of a microtiter plate, and two were frozen in liquid nitrogen in a well at the corresponding position of another microtiter plate. Fixed anthers were staged; then, the corresponding frozen anthers were pooled by stage and polyA+RNA was isolated from 20 anthers (RNA Micro-Quick Prep kit, Pharmacia Uppsila Sweden). Identical volumes of RNA from anthers at each pooled stage were subjected to electrophoresis on 1.2% agarose in MOPS buffer+formaldehyde. RNA samples were transferred by blotting to a nylon membrane, fixed by UV cross-linking (Stratalinker, Stratagene Inc., La Jolla), and hybridized to a 32P-labeled probe fragment consisting of all of the Ms45 cDNA coding region and 3' region. The results shown in FIG. 4 confirm steady state Ms45 transcript detectable in quartet through early uninucleate stages, and possibly as early as, but not earlier than, telophase II in meiosis. Either transcript levels resulting from Ms45 male tissue-preferred regulatory region activity during meiosis do not accumulate sufficiently to be detected by RNA hybridization, or the meiotic stage male tissue-preferred regulatory region activity observed in transient assays does not occur in plants.

Thus the Ms45 male tissue-preferred regulatory region (SEQ ID NO: 1) was characterized as having male tissue-preferred expression from at least quartet stage of anther development through quartet release, with lower-level expression possible in the meiotic and early uninucleate stages.

EXAMPLE 4

TATA Box Analysis

Within the 1388 bp fragment of DNA encoding the Ms45 male tissue-preferred regulatory region, the major start of transcription has been identified at +1, a minor start of transcription has been identified at −3 relative to the major start of transcription, and a putative TATA box has been identified at −33 (CATTAAA). It was noted that the sequence TAAAGAT at −30 could also be a candidate for the actual TATA box. This 1388bp fragment was operably linked to a reporter gene cassette comprising the luciferase coding region from firefly (Pareddy, et al., *Theoret. Appl. Genet.*; Vol. 77; pp. 521–526; (1989)) followed by the 3'-nontranslated region from the proteinase inhibitor II gene of potato. (An, G., et al., "Functional Analysis of the 3' Control Region of the Potato Wound-Inducible Proteinase Inhibitor II Gene"; *Plant Cell*; Vol. 1; pp. 115–122; (1989)).

One way that is well known in the art to analyze TATA boxes is through mutation. In another derivative, from one to six nucleotides of the putative TATA box were changed in a given derivative. A BGLII site was introduced at −38 altered the putative TATA box from CATTAAA to TAT-TAAA, which is a closer match to the canonical TATA box sequence TATATAA.

Figure 7:
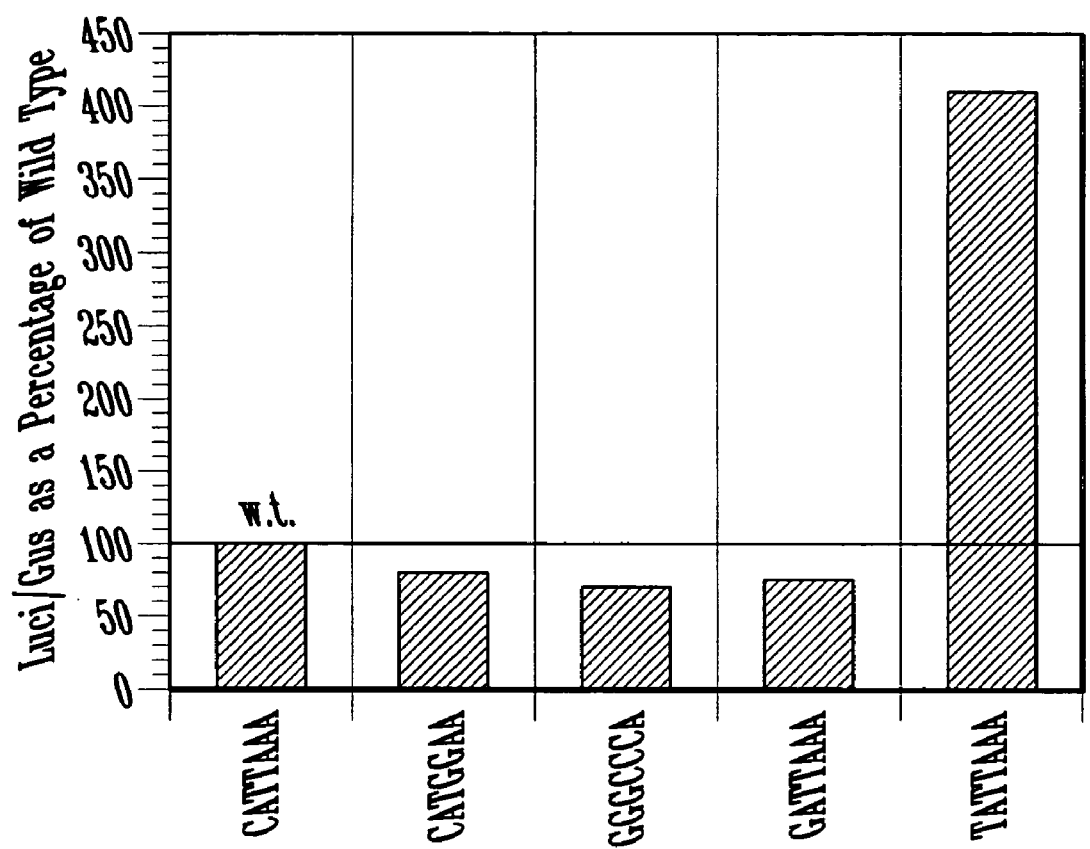
FIG. 7 shows the results of a mutational analysis of TATA box.

It will be appreciated by one skilled in the art that certain substitutions within the TATA box may affect the level of expression of the promoter without influencing tissue specificity. As shown in FIG. 7, the change in the TATA box associated with the BgIII site introduced at −38 dramatically increased transient expression levels in anthers and further suggests that the sequence at −33 is the authentic TATA box. Introduction of a BGLII site at −40, −43, −51 or −53 did not increase activity of the promoter (data not shown), proving that the increase observed in the −38 BGLII site introduction was unrelated to the BGLII site per se.

Other modifications of the putative TATA box were introduced to further test for its functionality. Alteration of the putative TATA box sequence from CATTAAA to GAT-TAAA, CATGGAA or GGGCCCA all reduced the transient expression level in anthers, further suggesting the importance of this sequence as a TATA box. Surprisingly, none of these mutations abolished transient activity; however, there have been reports of transient activity in other systems in the absence of a TATA-like sequence and even of TATA-less promoters (Guan, L., and J. G. Scandalios, *Plant J.*; Vol. 3; pp. 527–536; (1993); Close, P. S., "Cloning and Molecular Characterization of Two Nuclear Genes for *Zea mays* Mitochondrial Chaperonin 60"; (Dissertation); Iowa State University, Ames, Iowa; pp. 92, 128; (1993)).

While the foregoing describes preferred embodiments of the invention, it will be understood by those skilled in the art that variations and modifications may be made and still fall within the scope of the invention.

EXAMPLE 5

Essential Sequences

In determining the essential region of the MS45 promoter, the methods described in the specification supra were used. These methods are well known to one skilled in the art. In general, sequences are selectively mutated or deleted and the impact on expression then observed.

A series of 5' deletions in the Ms45 promoter were generated from −1394 to various existing restriction endonuclease cleavage sites to −221. (See FIG. 8) 5' deletions from −1394 to −195, −145 and −95 were generated by introduction of restriction sites by PCR. A series of 3' deletions, from −38 to −195, −145 and −95 were also generated. In these derivatives, a BglII cloning site was included that modified the putative TATA box from CAT-TAAA to TATTAAA, resulting in a higher level of reporter gene activity. Linker scanning mutations were generated by site-directed mutagenesis of the 5' deletion derivative to −195. Increments of 10 bp per mutant were altered along the length of the region upstream of the TATA box from −195 through −39, excepting the 5'-most substitution was 14 bp and the 3'-most substitution was 13 bp. All substitutions consisted of G and C residues and included an ApaI restriction site for ease of identifying the desired products of site-directed mutagenesis. Promoter derivatives were then fused to a luciferase reporter gene with a 3' nontranslated region from the Proteinase Inhibitor II (PinII) gene of *Solanum tuberosum* (An, G., Mitra, A., Choi, H. K., Costa, M. A., An, K., Thornburg, R. W. and Ryan, C. A. 1989. "Functional Analysis of the 3' Control Region of the Potato Wound-Inducible Proteinase Inhibitor II Gene" *Plant Cell* 1: 115–122.)

Promoter activity was measured by assaying luciferase gene expression following microprojectile bombardment of quartet- to early-uninucleate-staged anthers from corn. The luciferase gene was used as the marker gene. For control, a non-deleted Ms45 promoter:GUS:PinII-3' construct was also bombarded into anthers. Anthers were incubated for 16 hours at 27° C., and extracts were assayed for luciferase activity and β-glucuronidase (GUS) activity. Relative promoter activity in this assay is expressed as the luciferase activity of the mutant, normalized for the reference GUS activity, as a percent of luciferase activity for the full-length promoter (to −1394), also normalized for GUS activity. The activity of the −1394 promoter fragment was thus defined as 100%.

Figure 9:
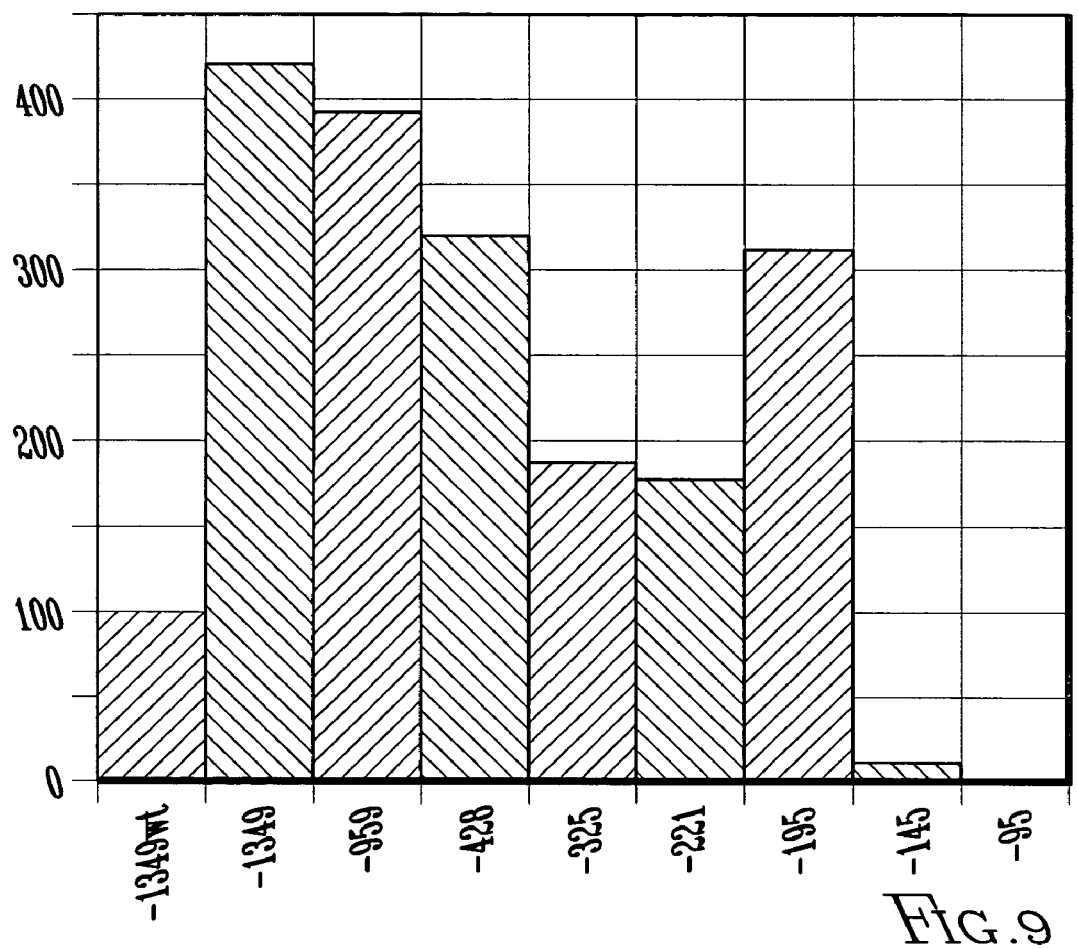
FIG. 9 is a graph representing the effect of 5' deletions (the deletion point shown on the x-axis) on activity of the MS45 promoter with BglII site number 3 (CAATCCATTA (SEQ ID NO: 7) to ATGATCTATTAAA (SEQ ID NO: 8)) (the y axis showing luciferase activity normalized to GUS as a percent of the wild type full length activity).
Figure 10:
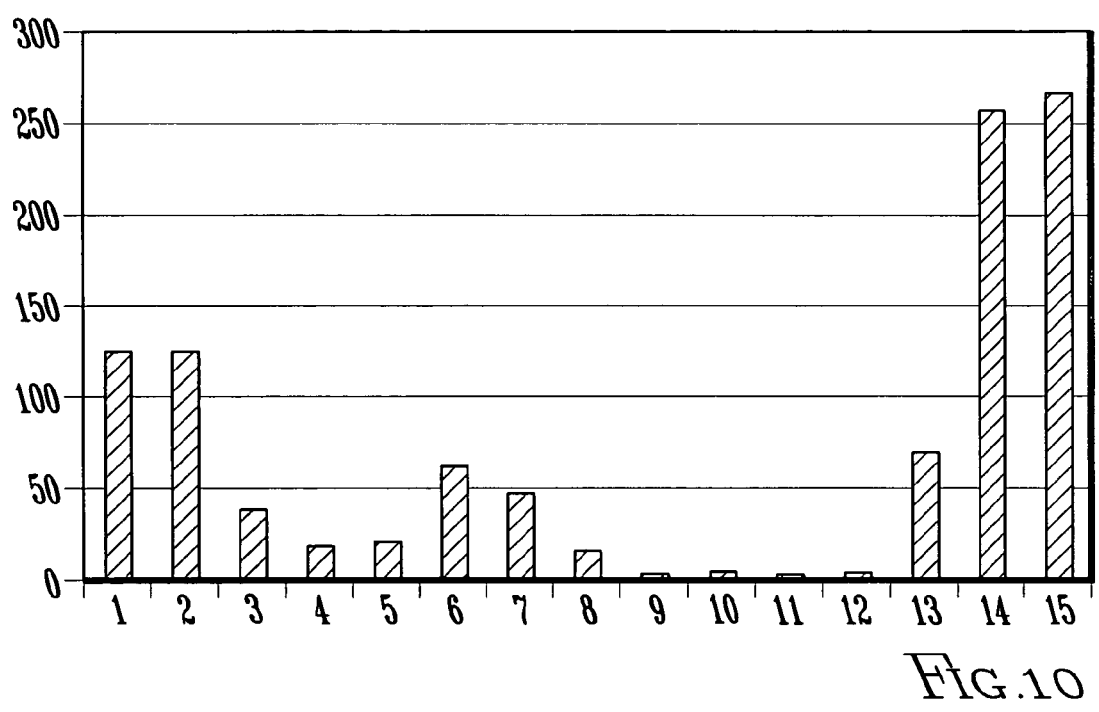
FIG. 10 is a graph representing the effect of linker scanning mutational analysis of the MS45 promoter, with the linker scanning mutant of the promoter (the mutation point referred to in FIG. 8 represented on the x-axis) fused to the luciferase reporter (the y axis showing luciferase activity normalized to GUS as a percent of the wild type full length activity).

Results are summarized below and in FIG. No. 8 which identifies the areas of mutation, and by the graphs of FIGS. No. 9 and 10, representing expression levels. FIG. 9 shows luciferase activity normalized to GUS as a percent of the wild type full length sequence, with the point of deletion in the sequence upstream of the TATA box identified. FIG. 10 also shows luciferase activity plotted against the linker scanning mutant of the MS45 promoter fused to the luciferase reporter. The data showed that significant activity was retained in the 5' deletion to −195, but that most of the promoter activity was lost by further deletion to −145. (See 5' deletion graph of FIG. 9). This indicates the presence of one or more important but not absolutely essential sequences between −145 and −195. The 5' deletion to −95 abolished activity, indicating that one or more essential promoter elements are likely to be present between −95 and −145. All of the 3' deletion derivatives generated from the MS45 promoter were inactive indicating that at least the region from −38 to −95 contains essential sequences. Further mutational analysis by linker scanning clarified the location of functional sequences in the Ms45 promoter. Notably, the region spanned by linker scanning mutations #09, 10, 11 and 12 (−111 through −72 relative to the start of transcription) appears to be essential, since each of these linker scanning mutations abolished promoter activity. (See linker scanning graph FIG. No. 10). Mutation of the 10 bp immediately upstream of this essential region resulted in a significant reduction in promoter activity, although not its elimination, suggesting that important sequences are present from −121 through −72. A similar reduction in activity was observed for linker scanning mutations #04 and 05 (and less dramatically for #03), which collectively span the region from −171 through −142. Mutational analysis of the Ms45 promoter has thus identified functional sequences between −171 and −142, and also between −121 and −72, with an essential region between −111 and −72.

While the foregoing describes preferred embodiments of the invention, it will be understood by those skilled in the art that variations and modifications may be made and still fall within the scope of the invention.

What is claimed is:

1. An isolated regulatory region comprising a nucleotide sequence selected from the group consisting of SEQ ID NO: 3, SEQ ID NO: 4, SEQ ID NO: 5 and SEQ ID NO: 6.

2. An expression cassette comprising the isolated regulatory region of claim 1, wherein said regulatory region is operably linked to an exogenous nucleic acid sequence.

3. An expression vector comprising the expression cassette of claim 2.

4. The expression vector of claim 3, wherein the vector further comprises a promoter operable linked to the regulatory region, wherein the promoter is selected from the group consisting of CaMV35S promoter, SGB6 promoter, SEQ ID NO: 1, SEQ ID NO: 2 or 5126 promoter.

5. The expression vector of claim 3, wherein the exogenous nucleic acid sequence disrupts male tissue function.

6. A plant cell comprising the expression vector of claim 3.

7. A method for preventing male fertility in a plant comprising: introducing into plant cells the expression vector of claim 5, and regenerating the transformed plant cells to a plant, thereby preventing male fertility of the plant.

8. The method of claim 7, further comprising growing the regenerated plant to a male sterile plant.

9. The method of claim 7 wherein the regulatory sequence is inducible.

10. A male sterile plant produced by the method of claim 8.

11. A method of producing a male fertile hybrid plant comprising cross-fertilizing the male sterile plant of claim 10 with a second plant comprising a second exogenous nucleic acid sequence encoding a protein that prevents the expression of the first exogenous sequence encoding a protein that disrupts male tissue function, thereby producing a male fertile hybrid plant.

12. A transformed plant regenerated from the plant cell of claim 6.

* * * * *

SEQUENCE LISTING

<160> NUMBER OF SEQ ID NOS: 24

<210> SEQ ID NO 1
<211> LENGTH: 1394
<212> TYPE: DNA
<213> ORGANISM: Zea mays

<400> SEQUENCE: 1

```
ccatggtgtc tctatgaaaa agatgagtac aatgtgtcta tatccgtttt cttagggtcc      60
cttcttctgc cttattactg actgaatcgg ggttacaaaa aacttccacg ggtgcatgat     120
ctccatgttc cacttctccc acctcgcgtt gcacatttct tggatgtcgg tggttcccat     180
ctgaccgagg cccatcagac acctttcggg acacccatca agggcctttc ggatggccca     240
cgagacgtat cgggtcgtgg tgatccaggg gatatatgtc ccccacaatc gtcacctata     300
ttattattct ttagatatta tttaattttt ggaaaaataa caaacttata cttttgtgta     360
gggcctcagc atagattttc gcttagggcc cagaaatgcg aggaccagcc atgtctagtg     420
tccactattg gcactaccca gaacaagatt taaaaaaata accaaagtaa ctaatccact     480
cgaaagctat catgtaatgt ttaaagaaac atctattaaa accacgatcc tcttaaaaaa     540
caagcatatt tcgaaagaga caaattatgt tacagtttac aaacatctaa gagcgacaaa     600
ttatatcgaa aggtaagcta tgacgttcag attttctttt ttcattcttg ttattttgtt     660
attgttttta tatacatttt cttctcttac aatagagtga ttttcttccg attttataaa     720
atgactataa agtcattttt atataagagc acgcatgtcg tagattctcg ttcaaaaatc     780
tttctgattt ttttaagagc tagtttggca accctgtttc tttcaaagaa ttttgatttt     840
ttcaaaaaaa attagtttat ttctctttta taaaatagaa aacacttaga aaaatagagt     900
tgccagacta gccctagaat gttttcccaa taaattacaa tcactgtgta taattatttg     960
gccagcccca taaattattt aaaccgaaac tgaaatcgag cgaaaccaaa tctgagctat    1020
```

```
ttctctagat tagtaaaaag ggagagagag aggaagaaat cagttttaag tcattgtccc    1080
tgagatgtgc ggtttggcaa cgatagccac cgtaatcata gctcataggt gcctacgtca    1140
ggttcggcag ctctcgtgtc atctcacatg gcatactaca tgcttgttca accgttcgtc    1200
ttgttccatc gtccaagcct tgcctattct gaaccaagag gatacctact cccaaacaat    1260
ccatcttact catgcaactt ccatgcaaac acgcacatat gtttcctgaa ccaatccatt    1320
aaagatcaca acagctagcg ttctcccgct agcttccctc tcctctgc cgatcttttt      1380 cgtccaccac catg                                                      1394

<210> SEQ ID NO 2
<211> LENGTH: 1394
<212> TYPE: DNA
<213> ORGANISM: Zea mays

<400> SEQUENCE: 2
ccatggtgtc tctatgaaaa agatgagtac aatgtgtcta tatccgtttt cttagggtcc      60
cttcttctgc cttattactg actgaatcgg ggttacaaaa aacttccacg ggtgcatgat     120
ctccatgttc cacttctccc acctcgcgtt gcacatttct tggatgtcgg tggttcccat     180
ctgaccgagg cccatcagac ccctttcggg acacccatca agggcctttc ggatggccca     240
cgagacgtat cgggtcgtgg tgatccaggg gatatatgtc ccccacaatc gtcacctata     300
ttattattct ttagatatta tttaattttt ggaaaaataa caaacttata cttttgtgta     360
gggcctcagc atagattttc gcttagggcc cagaaatgcg aggaccagcc atgtctagtg     420
tccactattg gcactaccca gaacaagatt taaaaaaata accaaagtaa ctaatccact     480
cgaaagctat catgtaatgt ttaaagaaac atctattaaa accacgatcc tcttaaaaaa     540
caagcatatt tcgaaagaga caaattatgt tacagtttac aaacatctaa gagcgacaaa     600
ttatatcgaa aggtaagcta tgacgttcag atttttcttt ttcattcttg ttattttgtt     660
attgttttta tatacatttt cttctcttac aatagagtga ttttcttccg attttataaa     720
atgactataa agtcattttt atataagagc acgcatgtcg tagattctcg ttcaaaaatc     780
tttctgattt ttttaagagc tagtttggca accctgtttc tttcaaagaa ttttgatttt     840
ttcaaaaaaa attagtttat tttctcttta taaatagaa acacttaga aaaatagagt       900 tgccagacta gccctagaat gttttcccaa taaattacaa tcactgtgta taattatttg     960
gccagcccca taaattattt aaaccgaaac tgaaatcgag cgaaaccaaa tctgagctat    1020
ttctctagat tagtaaaaag ggagagagag aggaagaaat cagttttaag tcattgtccc    1080
tgagatgtgc ggtttggcaa cgatagccac cgtaatcata gctcataggt gcctacgtca    1140
ggttcggcag ctctcgtgtc atctcacatg gcatactaca tgcttgttca accgttcgtc    1200
ttgttccatc gtccaagcct tgcctattct gaaccaagag gatacctact cccaaacaat    1260
ccatcttact catgcaactt ccatgcaaac acgcacatat gtttcctgaa cagatctatt    1320
aaagatcaca acagctagcg ttctcccgct agcttccctc tcctctgc cgatcttttt      1380 cgtccaccac catg                                                     1394

<210> SEQ ID NO 3
<211> LENGTH: 158
<212> TYPE: DNA
<213> ORGANISM: Zea mays

<400> SEQUENCE: 3
```

```
cgtgtcatct cacatggcat actacatgct tgttcaaccg ttcgtctttg ttccatcgtc    60
caagccttgc ctattctgaa ccaagaggat acctactccc aaacaatcca tcttactcat   120
gcaacttcca tgcaaacacg cacatatgtt tcctgaac                           158
```

<210> SEQ ID NO 4
<211> LENGTH: 30
<212> TYPE: DNA
<213> ORGANISM: Zea mays

<400> SEQUENCE: 4

```
catgcttgtt caaccgttcg tcttgttcca                                     30
```

<210> SEQ ID NO 5
<211> LENGTH: 50
<212> TYPE: DNA
<213> ORGANISM: Zea mays

<400> SEQUENCE: 5

```
ctgaaccaag aggataccta ctcccaaaca atccatctta ctcatgcaac               50
```

<210> SEQ ID NO 6
<211> LENGTH: 40
<212> TYPE: DNA
<213> ORGANISM: Zea mays

<400> SEQUENCE: 6

```
aggataccta ctcccaaaca atccatctta ctcatgcaac                          40
```

<210> SEQ ID NO 7
<211> LENGTH: 11
<212> TYPE: DNA
<213> ORGANISM: Artificial Sequence
<220> FEATURE:
<223> OTHER INFORMATION: Description of Artificial Sequence:
      Illustrative DNA

<400> SEQUENCE: 7

```
caatccatta a                                                         11
```

<210> SEQ ID NO 8
<211> LENGTH: 13
<212> TYPE: DNA
<213> ORGANISM: Artificial Sequence
<220> FEATURE:
<223> OTHER INFORMATION: Description of Artificial Sequence:
      Illustrative DNA

<400> SEQUENCE: 8

```
atgatctatt aaa                                                       13
```

<210> SEQ ID NO 9
<211> LENGTH: 255
<212> TYPE: DNA
<213> ORGANISM: Zea mays

<400> SEQUENCE: 9

```
gcggccgcgg atcccgtgtc atctcacatg gcatactaca tgcttgttca accgttcgtc    60
ttgttccatc gtccaagcct tgcctattct gaaccaagag gatacctact cccaaacaat   120
ccatcttact catgcaactt ccatgcaaac acgcacatat gtttcctgaa cagatctatt   180
aaagatcaca acagctagcg ttctcccgct agcttccctc tcctctgc cgatcttttt     240 cgtccaccac catgg                                                    255
```

<210> SEQ ID NO 10
<211> LENGTH: 14
<212> TYPE: DNA
<213> ORGANISM: Zea mays

<400> SEQUENCE: 10
gcgcgggccc gcgc                                                          14

<210> SEQ ID NO 11
<211> LENGTH: 10
<212> TYPE: DNA
<213> ORGANISM: Zea mays

<400> SEQUENCE: 11
gccgggcccg                                                               10

<210> SEQ ID NO 12
<211> LENGTH: 10
<212> TYPE: DNA
<213> ORGANISM: Zea mays

<400> SEQUENCE: 12
gcgcgggccc                                                               10

<210> SEQ ID NO 13
<211> LENGTH: 10
<212> TYPE: DNA
<213> ORGANISM: Zea mays

<400> SEQUENCE: 13
gcgggcccgc                                                               10

<210> SEQ ID NO 14
<211> LENGTH: 10
<212> TYPE: DNA
<213> ORGANISM: Zea mays

<400> SEQUENCE: 14
cgggcccggc                                                               10

<210> SEQ ID NO 15
<211> LENGTH: 10
<212> TYPE: DNA
<213> ORGANISM: Zea mays

<400> SEQUENCE: 15
cgcgggcccg                                                               10

<210> SEQ ID NO 16
<211> LENGTH: 10
<212> TYPE: DNA
<213> ORGANISM: Zea mays

<400> SEQUENCE: 16
gcgcgggccc                                                               10

<210> SEQ ID NO 17
<211> LENGTH: 10
<212> TYPE: DNA
<213> ORGANISM: Zea mays

<400> SEQUENCE: 17

-continued ggccgggccc                                                                                     10

<210> SEQ ID NO 18
<211> LENGTH: 10
<212> TYPE: DNA
<213> ORGANISM: Zea mays

<400> SEQUENCE: 18
gccggggccc                                                                                     10

<210> SEQ ID NO 19
<211> LENGTH: 10
<212> TYPE: DNA
<213> ORGANISM: Zea mays

<400> SEQUENCE: 19
gcgggcccgc                                                                                     10

<210> SEQ ID NO 20
<211> LENGTH: 10
<212> TYPE: DNA
<213> ORGANISM: Zea mays

<400> SEQUENCE: 20
gcgggcccgc                                                                                     10

<210> SEQ ID NO 21
<211> LENGTH: 10
<212> TYPE: DNA
<213> ORGANISM: Zea mays

<400> SEQUENCE: 21
gggcccgccg                                                                                     10

<210> SEQ ID NO 22
<211> LENGTH: 10
<212> TYPE: DNA
<213> ORGANISM: Zea mays

<400> SEQUENCE: 22
cgggcccgcg                                                                                     10

<210> SEQ ID NO 23
<211> LENGTH: 10
<212> TYPE: DNA
<213> ORGANISM: Zea mays

<400> SEQUENCE: 23
cgggcccgcg                                                                                     10

<210> SEQ ID NO 24
<211> LENGTH: 13
<212> TYPE: DNA
<213> ORGANISM: Zea mays

<400> SEQUENCE: 24
gggcccggcc gcg                                                                                 13